(12) United States Patent
Hyde et al.

(10) Patent No.: US 6,632,522 B1
(45) Date of Patent: Oct. 14, 2003

(54) BLENDED PRESSURE-SENSITIVE ADHESIVES

(75) Inventors: Patrick Darby Hyde, Burnsville, MN (US); Roy Wong, White Bear Lake, MN (US); Dennis Louis Krueger, Hudson, WI (US); Robert W. G. Shipman, Oakdale, MN (US); David James Yarusso, Shoreview, MN (US); Felix P. Lau, Austin, MN (US); Eumi Pyun, Austin, TX (US); Pamela S. Tucker, Austin, TX (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/091,683

(22) PCT Filed: Aug. 16, 1996

(86) PCT No.: PCT/US96/13364

§ 371 (c)(1),
(2), (4) Date: Nov. 24, 2000

(87) PCT Pub. No.: WO97/23577

PCT Pub. Date: Jul. 3, 1997

Related U.S. Application Data

(63) Continuation-in-part of application No. 08/577,603, filed on Dec. 22, 1995, now abandoned, which is a continuation-in-part of application No. 08/578,010, filed on Dec. 22, 1995, now abandoned, which is a continuation-in-part of application No. 08/390,780, filed on Feb. 16, 1995, now abandoned.

(51) Int. Cl.[7] .............................. B05D 5/10; B32B 7/12; B32B 5/00; C08L 33/04; C08L 53/02

(52) U.S. Cl. ............ 428/355 R; 428/343; 428/355 BL; 428/355 AC; 524/271; 524/505; 524/526; 427/208.4

(58) Field of Search .............................. 428/355 R, 343, 428/355 BL, 355 AC; 524/481, 505, 526, 236, 271; 427/208.4

(56) References Cited

U.S. PATENT DOCUMENTS

| | | | |
|---|---|---|---|
| 2,736,721 A | 2/1956 | Dexter .......................... 260/42 |
| 2,956,904 A | 10/1960 | Hendricks ..................... 117/93 |
| RE24,906 E | 12/1960 | Uhlrich ........................ 206/59 |
| 3,246,049 A | 4/1966 | Webber ........................ 260/826 |
| 3,890,407 A | 6/1975 | Briggs, Jr. et al. ........... 260/878 |
| 3,975,463 A | 8/1976 | Hirata et al. ................. 260/897 |
| 4,107,233 A | 8/1978 | Hansen ........................ 260/876 |
| 4,243,500 A | 1/1981 | Glennon ................. 204/159.12 |
| 4,288,358 A | 9/1981 | Trotter et al. ............... 260/31.8 |
| 4,388,349 A | 6/1983 | Korpman et al. ........ 427/208.4 |
| 4,410,482 A | 10/1983 | Subramanian ............... 264/515 |
| 4,438,232 A | 3/1984 | Lee .............................. 524/272 |
| 4,444,817 A | 4/1984 | Subramanian ................ 428/36 |
| 4,554,324 A | 11/1985 | Husman et al. .............. 525/301 |
| 4,619,979 A | 10/1986 | Kotnour et al. ............... 526/88 |
| 4,699,842 A | 10/1987 | Jorgensen et al. ........... 428/343 |
| 4,732,808 A | 3/1988 | Krampe et al. .............. 428/355 |
| 4,810,523 A | 3/1989 | Williams et al. .............. 427/36 |
| 4,833,179 A | 5/1989 | Young et al. ................. 522/183 |
| 4,835,217 A | 5/1989 | Jorgensen et al. ............. 525/93 |
| 4,912,169 A | 3/1990 | Whitmire et al. ............ 525/221 |
| 4,952,650 A | 8/1990 | Young et al. ............ 427/208.9 |
| 4,994,267 A | 2/1991 | Sablotsky .................... 428/484 |
| 5,143,972 A | 9/1992 | Groves ......................... 525/71 |
| 5,198,064 A | 3/1993 | Tani et al. ................... 428/247 |
| 5,202,361 A | 4/1993 | Zimmerman et al. ....... 522/120 |
| 5,206,288 A | 4/1993 | Gosiewski et al. ........... 525/83 |
| 5,209,971 A | 5/1993 | Babu et al. .................. 428/343 |
| 5,214,119 A | 5/1993 | Leihr et al. ................... 528/28 |
| 5,217,794 A | 6/1993 | Schrenk ....................... 420/230 |
| 5,229,206 A | 7/1993 | Groves ......................... 428/344 |
| 5,230,701 A | 7/1993 | Meyer et al. ................. 602/76 |
| 5,257,491 A | 11/1993 | Rouyer et al. ................ 53/428 |
| 5,266,399 A | 11/1993 | Babu et al. .................. 428/343 |
| 5,284,889 A | 2/1994 | Pyun et al. ................... 824/94 |
| 5,286,781 A | 2/1994 | Gotoh et al. ................. 524/505 |
| 5,290,842 A | 3/1994 | Sasaki et al. ................. 524/271 |
| 5,296,561 A | 3/1994 | Babu et al. .................. 525/342 |
| 5,300,291 A | 4/1994 | Sablotsky et al. ............. 424/78 |
| 5,382,451 A | 1/1995 | Johnson et al. .......... 427/208.4 |
| 5,385,783 A | 1/1995 | Patel et al. .................. 428/153 |
| 5,462,538 A | * 10/1995 | Korpman .................... 604/358 |
| 5,866,249 A | * 2/1999 | Yarusso et al. .............. 428/355 |

FOREIGN PATENT DOCUMENTS

| | | |
|---|---|---|
| DE | 2 241 829 | 3/1974 |
| EP | 0 312 228 | 4/1989 |
| EP | 0 349 216 A1 | 1/1990 |
| EP | 0 352 901 | 1/1990 |
| EP | 0 437 068 A2 | 12/1990 |
| EP | 0 457 566 | 11/1991 |
| JP | 58093773 | 11/1981 |
| JP | SHO 60 226579 | 11/1985 |
| JP | 2-206671 | 8/1990 |
| JP | HEI 4-18344 | 1/1992 |
| JP | 4110377 | 4/1992 |
| JP | HEI 5-98223 | 4/1993 |
| JP | 07003235 | 1/1995 |
| NO | B 168832 | 4/1989 |
| WO | WO 93/07228 | 4/1993 |
| WO | WO 93/20165 | 10/1993 |
| WO | WO 93/23224 | 11/1993 |
| WO | WO 94/24221 | 10/1994 |
| WO | WO 95/25774 | 9/1995 |
| WO | WO 96/25469 | 8/1996 |
| WO | WO 96/26251 | 8/1996 |
| WO | WO 97 23577 A | 7/1997 |

* cited by examiner

Primary Examiner—Tae H. Yoon
(74) Attorney, Agent, or Firm—James V. Lilly

(57) ABSTRACT

A pressure-sensitive adhesive comprising a blend of at least two components, wherein the first component is at least one pressure-sensitive adhesive and second component is at least one thermoplastic material, wherein the components form a blended composition having more than one domain and, wherein one domain is substantially continuous (generally, the pressure-sensitive adhesive) and the other domain is substantially fibrillous to schistose (generally, the thermoplastic material). The second component can be (a) at least one thermoplastic elastomer, (b) at least one elastomer with a tackifying resin or (c) at least one elastomer.

44 Claims, 11 Drawing Sheets

BLENDED PRESSURE-SENSITIVE ADHESIVES

RELATED APPLICATIONS

This application is the U.S. national stage of PCT/US96/13364. It is a continuation-in-part of (1) application Ser. No. 08/577,603, filed Dec. 22, 1995, now abandoned, which is incorporated herein by reference, and (2) application Ser. No. 08/578,010, filed Dec. 22, 1995, which is incorporated herein by reference, and which is a continuation-in-part of application Ser. No. 08/390,780, filed Feb. 16, 1995, now abandoned.

TECHNICAL FIELD

This invention relates to pressure-sensitive adhesive compositions, and, more particularly, to pressure-sensitive adhesive compositions formed from at least two polymeric materials at least one of which is a pressure-sensitive adhesive, and to methods of making blended pressure-sensitive adhesives and to adhesive coated articles.

BACKGROUND OF THE INVENTION

There is an ongoing need to modify pressure-sensitive adhesives to meet the needs of new applications. In general, when additives are incorporated into pressure-sensitive adhesives to modify their properties, care must be taken to avoid a loss in peel adhesion or shear strength. This has prevented a wide use of thermoplastic materials as modifiers.

Major classes of pressure-sensitive adhesives include tackified natural rubbers; synthetic rubbers such as butyl rubber; and tackified linear, radial, star, and branched and tapered styrene block copolymers, such as styrene-butadiene, styrene-ethylene/butylene and styrene-isoprene; polyurethanes; polyvinyl ethers; acrylics, especially those having long chain alkyl groups; poly-α-olefins; and silicones.

Generally, when additives are used to alter properties of pressure-sensitive adhesives, the additives need to be miscible with the pressure-sensitive adhesive or to form homogeneous blends at the molecular level. Some types of pressure-sensitive adhesives have been modified with tackified thermoplastic elastomers, thermoplastics, and elastomers. For example, thermoplastic materials have been added to polymerized hot melt acrylic pressure-sensitive adhesives wherein the thermoplastic is a packaging material or recyclable tape backings. In these cases, the type and amount of thermoplastic material is controlled so that the thermoplastic material can function as a packaging material while avoiding degradation of the adhesive properties of the pressure-sensitive adhesive.

However, more often than not when a non-tacky thermoplastic additive is blended with a pressure-sensitive adhesive, reduction of the overall adhesive properties of the blend (as compared to the pressure-sensitive adhesive only) are observed. Thermoplastic polymers have been added to styrene block copolymer adhesives to reduce the tack of the resulting pressure-sensitive adhesives for application of protective sheets to large area surfaces.

Pressure-sensitive adhesives, whether modified or not have been used for more than half a century for a variety of purposes. Generally, pressure-sensitive adhesives are used in tapes wherein a tape comprises a backing, or substrate, and a pressure-sensitive adhesive. Typically, a pressure-sensitive adhesive adheres with no more than applied finger pressure and can be permanently tacky.

In the medical field, pressure-sensitive adhesive tapes are used for many different applications in the hospital and health areas. For most applications, tapes are applied directly to a patient's skin. It is important that the pressure-sensitive adhesive tape be compliant and non-irritating to the skin, as well as adhering to the skin without causing damage to the skin when the tape or adhesive coated article is removed. A particularly useful medical application for pressure-sensitive adhesive tapes and articles is in the field of transdermal patches. Such patches can be used as drug transport membranes or to attach drug transport membranes to skin.

Although pressure-sensitive adhesive tapes and articles are widely used in the medical field, pressure-sensitive adhesive tapes and articles find widespread use in many other applications. For example, transfer tapes can be used to adhere two surfaces together such as the flaps of packing material or fabric to a surface. However, transfer tape adhesives generally have little tensile strength and one solution has been to add glass fibers to provide tensile strength.

Another use is in the field of labels, which require a large variety of pressure-sensitive adhesives due to a wide variety of surfaces. However, the pressure-sensitive adhesives must be able to be cut easily without stringing out or oozing to permit efficient manufacturing processes.

Pressure-sensitive adhesives require a delicate balance of viscous and elastic properties that result in a four-fold balance of adhesion, cohesion, stretchiness and elasticity. Pressure-sensitive adhesives generally comprise elastomers that are either inherently tacky, or elastomers or thermoplastic elastomers that are tackified with the addition of tackifying resins.

SUMMARY OF THE INVENTION

In one aspect, the present invention provides a pressure-sensitive adhesive comprising a blend of at least two components, wherein the first component is at least one pressure-sensitive adhesive and the second component is at least one thermoplastic material, wherein the components form a blended composition having more than one domain and, wherein one domain is substantially continuous (generally, the pressure-sensitive adhesive) and the other domain is substantially fibrillous to schistose (generally, the thermoplastic material).

Alternatively, the second component can be (a) at least one thermoplastic elastomer, as described in Ser. No. 08/578,010, filed Dec. 22, 1995 with a common assignee, (b) at least one elastomer with a tackifying resin as described in Ser. No. 08/577,603, filed Dec. 22, 1995 with a common assignee, or (c) at least one elastomer.

Advantageously, blended pressure-sensitive adhesives of the present invention provide adhesives having one or more of the following properties. These properties are improvements over a pressure-sensitive adhesive prior to blending it with a thermoplastic material. These properties include:

(1) a peel adhesion greater than and shear strength similar to that of the pressure-sensitive adhesive component if used alone,
(2) a shear strength greater than and peel adhesion similar to that of the pressure-sensitive adhesive component if used alone,
(3) an anisotropic peel adhesion,
(4) an anisotropic shear strength, and
(5) a tensile stress in the down-web direction that is at least 2 times greater than the tensile stress in the cross-web direction for all elongations up to the break elongation.

The pressure-sensitive adhesive component should be hot-melt processable and meet the Dahlquist criteria as described in Handbook of Pressure-sensitive Adhesive Technology, Edited by D. Satas, pg. 172, (1989) at use temperatures. Typically, the pressure-sensitive adhesive component comprises 30–98 weight percent of the composition, preferably 40–95 weight percent and more preferably 60–95 weight percent. Furthermore, the pressure-sensitive adhesive component could be a single pressure-sensitive adhesive or the pressure-sensitive adhesive could be a mixture of several pressure-sensitive adhesives.

The thermoplastic material component is typically a high polymer that can soften when exposed to heat and can return to the solid state when cooled to room temperature. Useful thermoplastic materials are fiber formers and are essentially immiscible in the pressure-sensitive adhesive component at use temperature, although the thermoplastic may be miscible in the pressure-sensitive adhesive at processing temperatures. Typically, the thermoplastic material component comprises 2–70 weight percent, preferably 5–60 weight percent and more preferably 5–40 weight percent. Furthermore, the thermoplastic material component could be a single thermoplastic material or the thermoplastic material could be a mixture of several thermoplastic materials.

In another aspect, a melt process for blended pressure-sensitive adhesives is described. Both components are melt mixed in a vessel and formed into a blended pressure-sensitive adhesive composition. The forming step is either (1) extruding the melt blended components under shear and/or extensional flow conditions or (2) extruding and drawing the melt blend. The formed composition is then cooled.

Also provided are pressure-sensitive adhesive coated tapes and articles.

DESCRIPTION OF THE PREFERRED EMBODIMENT(S)

Figure 1:
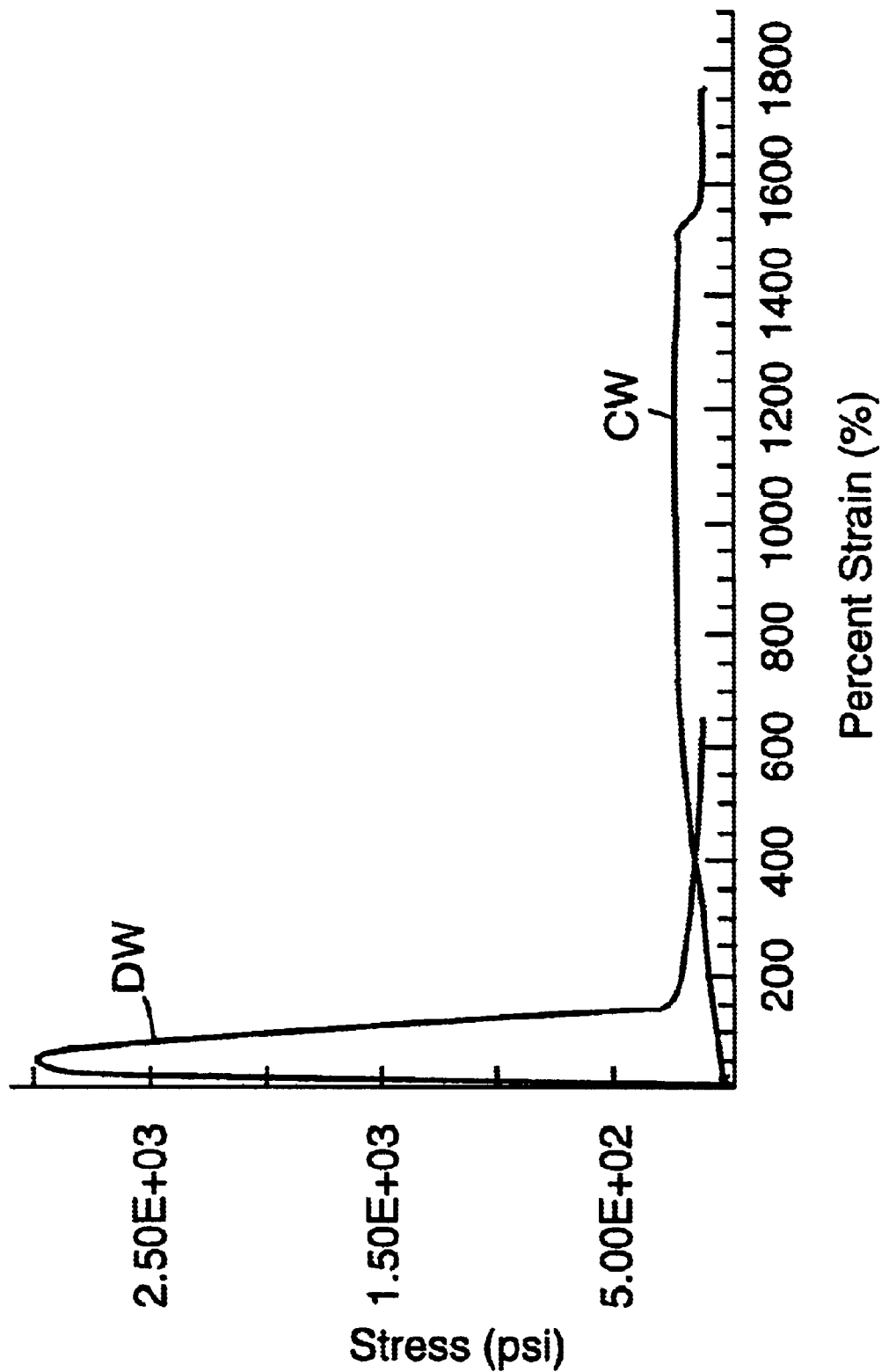
FIG. 1 is a stress-strain plot of the pressure-sensitive adhesive layer of Example 31 in both the down-web and cross-web directions.
Figure 2:
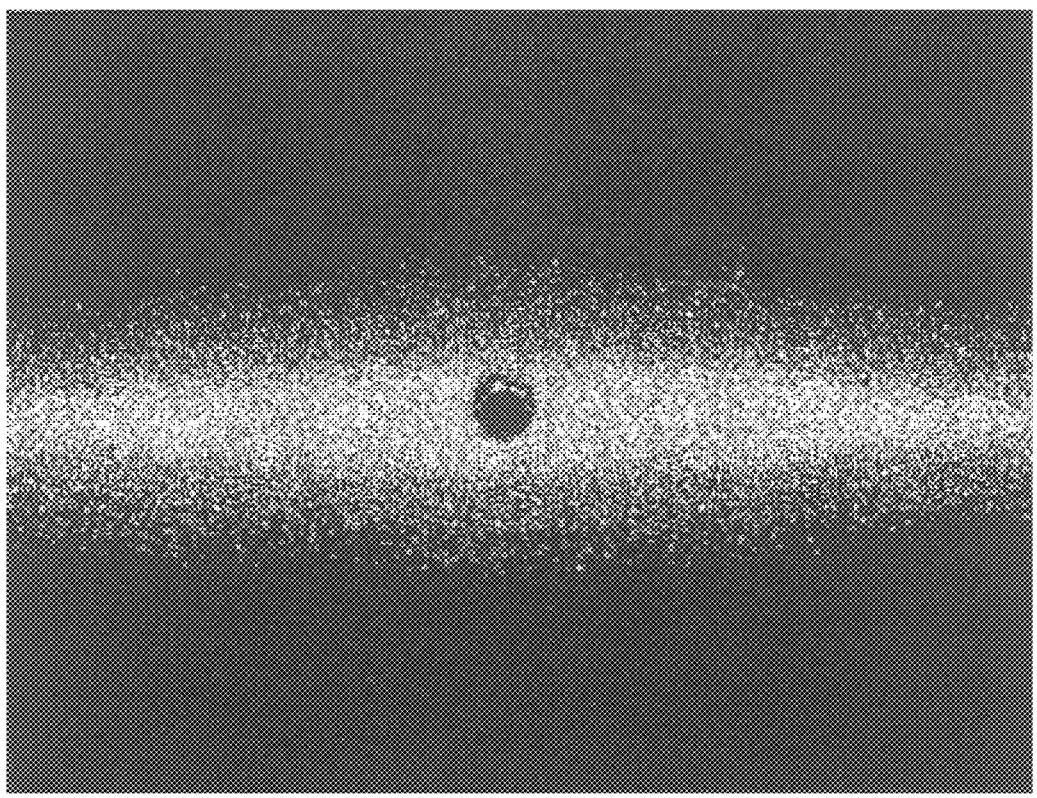
FIG. 2 is the light scattering pattern for the pressure-sensitive adhesive layer of Example 39 using the laser light scattering test.
Figure 3:
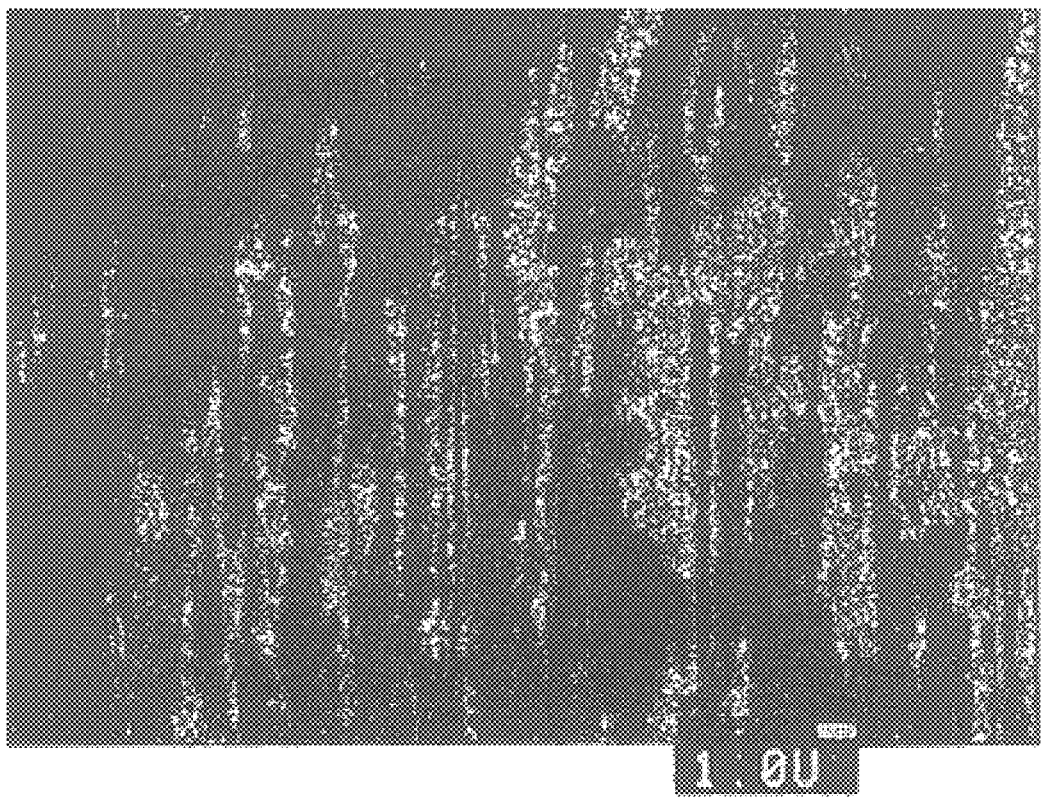
FIG. 3 is a cross-sectional view in the down-web direction of the pressure-sensitive adhesive layer of Example 44 at 4000× using scanning electron microscopy (SEM).

The present invention provides a pressure-sensitive adhesive comprising a blend of at least two components, wherein the first component is at least one pressure-sensitive adhesive and the second component is at least one thermoplastic material, wherein the components form a blended composition having more than one domain. Alternatively, the second component can be (a) at least one thermoplastic elastomer, as described in Ser. No. 08/578,010, filed Dec. 22, 1995 with a common assignee, (b) at least one elastomer with a tackifying resin as described in Ser. No. 08/577,603, filed Dec. 22, 1995 with a common assignee, or (c) at least one elastomer.

The pressure-sensitive adhesive component can be any material that has pressure-sensitive adhesive properties as described in The Handbook of Pressure-sensitive Adhesives, page 172, paragraph 1, 1989. Further, useful pressure-sensitive adhesives are hot-melt processable and meet the Dahlquist criteria at use temperatures. Typically, the pressure-sensitive adhesive component comprises 30–98 weight percent, preferably 40–95 weight percent and more preferably 60–95 weight percent. Furthermore, the pressure-sensitive adhesive component could be a single pressure-sensitive adhesive or the pressure-sensitive adhesive could be a mixture of several pressure-sensitive adhesives.

Pressure-sensitive adhesives useful in the present invention include tackified natural rubbers, synthetic rubbers, tackified styrene block copolymers, polyvinyl ethers, acrylics, poly-α-olefins, and silicones.

Useful natural rubber pressure-sensitive adhesives generally contain masticated natural rubber, from 25 parts to 300 parts of one or more tackifying resins to 100 parts of natural rubber, and typically from 0.5 to 2.0 parts of one or more antioxidants. Natural rubber may range in grade from a light pale crepe grade to a darker ribbed smoked sheet and includes such examples as CV-60, a controlled viscosity rubber grade and SMR-5, a ribbed smoked sheet rubber grade. Tackifying resins used with natural rubbers generally include but are not limited to wood rosin and its hydrogenated derivatives; terpene resins of various softening points, and petroleum-based resins, such as, the ESCOREZ™ 1300 series of C5 aliphatic olefin-derived resins from Exxon. Antioxidants are used to retard the oxidative attack on natural rubber, which can result in loss of the cohesive strength of the natural rubber adhesive. Useful antioxidants include but are not limited to amines, such as N-N' di-β-naphthyl-1,4-phenylenediamine, available as AgeRite D; phenolics, such as 2,5-di-(t-amyl)hydroquinone, available as Santovar AT™, available from Monsanto Chemical Co., tetrakis[methylene 3-(3',5'-di-tert-butyl-4'-hydroxyphenyl) propianate]methane, available as IRGANOX™ 1010 from Ciba-Geigy Corp., and 2-2'-methylenebis(4-methyl-6-tert butyl phenol), available as Antioxidant 2246; and dithiocarbamates, such as zinc dithiodibutyl carbamate. Other materials can be added to natural rubber adhesives for special purposes, wherein the additions can include plasticizers, pigments, and curing agents to partially vulcanize the pressure-sensitive adhesive.

Another useful class of pressure-sensitive adhesives are those comprising synthetic rubber. Such adhesives are generally rubbery elastomers, which are either self-tacky or non tacky and require tackifiers.

Self-tacky synthetic rubber pressure-sensitive adhesives include for example, butyl rubber, a copolymer of isobutylene with less than 3 percent isoprene, polyisobutylene, a homopolymer of isoprene, polybutadiene, or styrene/butadiene rubber. Butyl rubber pressure-sensitive adhesives often contain an antioxidant such as zinc dibutyl dithiocarbamate. Polyisobutylene pressure-sensitive adhesives do not usually contain antioxidants. Synthetic rubber pressure-sensitive adhesives, which generally require tackifiers, are also generally easier to melt process. They comprise polybutadiene or styrene/butadiene rubber, from 10 parts to 200 parts of a tackifier, and generally from 0.5 to 2.0 parts per 100 parts rubber of an antioxidant such as IRGANOX™ 1010. An example of a synthetic rubber is AMERIPOL™ 1011A, a styrene/butadiene rubber available from BF Goodrich. Tackifiers that are useful include derivatives of rosins such as FORAL™ 85, a stabilized rosin ester from Hercules, Inc., the SNOWTACK™ series of gum rosins from Tenneco, and the AQUATAC series of tall oil rosins from Sylvachem; and synthetic hydrocarbon resins such as the PICCOLYTE™ A series, polyterpenes from Hercules, Inc., the ESCOREZ™ 1300 series of C5 aliphatic olefin-derived resins and the ESCOREZ™ 2000 Series of C9 aromatic/aliphatic olefin-derived resins. Other materials can be added for special purposes, including hydrogenated butyl rubber, pigments, plasticizers, liquid rubbers, such as VISTANEX™ LMMH polyisobutylene liquid rubber available from Exxon, and curing agents to vulcanize the adhesive partially.

Styrene block copolymer pressure-sensitive adhesives generally comprise elastomers of the A—B or A—B—A type, where A represents a thermoplastic polystyrene block and B represents a rubbery block of polyisoprene, polybutadiene, or poly(ethylene/butylene), and resins. Examples of the various block copolymers useful in block copolymer pressure-sensitive adhesives include linear, radial, star and tapered styrene-isoprene block copolymers such as KRATON™ D1107P, available from Shell Chemical Co., and EUROPRENE™ SOL TE 9110, available from EniChem Elastomers Americas, Inc.; linear styrene-(ethylene-butylene) block copolymers such as KRATON™ G1657, available from Shell Chemical Co.; linear styrene-(ethylene-propylene) block copolymers such as KRATON™ G1750X, available from Shell Chemical Co.; and linear, radial, and star styrene-butadiene block copolymers such as KRATON™ D1118X, available from Shell Chemical Co., and EUROPRENE™ SOL TE 6205, available from EniChem Elastomers Americas, Inc. The polystyrene blocks tend to form domains in the shape of spheroids, cylinders, or plates that causes the block copolymer pressure-sensitive adhesives to have two phase structures. Resins that associate with the rubber phase generally develop tack in the pressure-sensitive adhesive. Examples of rubber phase associating resins include aliphatic olefin-derived resins, such as the ESCOREZ™ 1300 series and the WINGTACK™ series, available from Goodyear; rosin esters, such as the FORAL™ series and the STAYBELITE™ Ester 10, both available from Hercules, Inc.; hydrogenated hydrocarbons, such as the ESCOREZ™ 5000 series, available from Exxon; polyterpenes, such as the PICCOLYTE™ A series; and terpene phenolic resins derived from petroleum or terpentine sources, such as PICCOFYN™ A100, available from Hercules, Inc. Resins that associate with the thermoplastic phase tend to stiffen the pressure-sensitive adhesive. Thermoplastic phase associating resins include polyaromatics, such as the PICCO™ 6000 series of aromatic hydrocarbon resins, available from Hercules, Inc.; coumarone-indene resins, such as the CUMAR™ series, available from Neville; and other high-solubility parameter resins derived from coal tar or petroleum and having softening points above about 85° C., such as the AMOCO™ 18 series of alphamethyl styrene resins, available from Amoco, PICCOVAR™ 130 alkyl aromatic polyindene resin, available from Hercules, Inc., and the PICCOTEX™ series of alphamethyl styrene/vinyl toluene resins, available from Hercules. Other materials can be added for special purposes, including rubber phase plasticizing hydrocarbon oils, such as, TUF-FLO™ 6056, available from Lydondell Petrochemical Co., Polybutene-8 from Chevron, KAYDOL™, available from Witco, and SHELLFLEX™ 371, available from Shell Chemical Co.; pigments; antioxidants, such as IRGANOX™ 1010 and IRGANOX™ 1076, both available from Ciba-Geigy Corp., BUTAZATE™, available from Uniroyal Chemical Co., CYANOX™LDTP, available from American Cyanamid, and BUTASAN™, available from Monsanto Co.; antiozonants, such as NBC, a nickel dibutyldithiocarbamate, available from DuPont; liquid rubbers such as VISTANEX™ LMMH polyisobutylene rubber; and ultraviolet light inhibitors, such as IRGANOX™ 1010 and TINUVIN™ P, available from Ciba-Geigy Corp.

Polyvinyl ether pressure-sensitive adhesives are generally blends of homopolymers of vinyl methyl ether, vinyl ethyl ether or vinyl iso-butyl ether, or blends of homopolymers of vinyl ethers and copolymers of vinyl ethers and acrylates to achieve desired pressure-sensitive properties. Depending on the degree of polymerization, homopolymers may be viscous oils, tacky soft resins or rubber-like substances. Polyvinyl ethers used as raw materials in polyvinyl ether adhesives include polymers based on: vinyl methyl ether such as LUTANOL™ M 40, available from BASF, and GANTREZ™ M 574 and GANTREZ™ M 555, available from ISP Technologies, Inc.; vinyl ethyl ether such as LUTANOL™ A 25, LUTANOL™ A 50 and LUTANOL™ A 100; vinyl isobutyl ether such as LUTANOL™ I 30, LUTANOL™ I 60, LUTANOL™ IC, LUTANOL™ I 60D and LUTANOL™ I 65D; methacrylate/vinyl isobutyl ether/acrylic acid such as ACRONAL™ 550 D, available from BASF. Antioxidants useful to stabilize the polyvinylether pressure-sensitive adhesive include, for example, IONOX™ 30 available from Shell, IRGANOX™ 1010 available from Ciba-Geigy, and Antioxidant ZKF available from Bayer Leverkusen. Other materials can be added for special purposes as described in BASF literature including tackifier, plasticizer and pigments.

Acrylic pressure-sensitive adhesives generally have a glass transition temperature of about −20° C. or less and may comprise from 100 to 80 weight percent of a $C_3$–$C_{12}$ alkyl ester component such as, for example, isooctyl acrylate, 2-ethyl-hexyl acrylate and n-butyl acrylate and from 0 to 20 weight percent of a polar component such as, for example, acrylic acid, methacrylic acid, ethylene vinyl acetate, N-vinyl pyrrolidone and styrene macromer. Preferably, the acrylic pressure-sensitive adhesives comprise from 0 to 20 weight percent of acrylic acid and from 100 to 80 weight percent of isooctyl acrylate. The acrylic pressure-sensitive adhesives may be self-tacky or tackified. Useful tackifiers for acrylics are rosin esters such as FORAL™ 85, available from Hercules, Inc., aromatic resins such as PICCOTEX™ LC-55WK, aliphatic resins such as PICCOTAC™ 95, available from Hercules, Inc., and terpene resins such as α-pinene and β-pinene, available as PICCOLYTE™ A-115, and ZONAREZ™ B-100 from Arizona Chemical Co. Other materials can be added for special purposes, including hydrogenated butyl rubber, pigments, and curing agents to vulcanize the adhesive partially.

Poly-α-olefin pressure-sensitive adhesives, also called a poly(1-alkene) pressure-sensitive adhesives, generally comprise either a substantially uncrosslinked polymer or a uncrosslinked polymer that may have radiation activatable functional groups grafted thereon as described in U.S. Pat. No. 5,209,971 (Babu, et al) which is incorporated herein by reference. The poly-α-olefin polymer may be self tacky and/or include one or more tackifying materials. If uncrosslinked, the inherent viscosity of the polymer is generally between about 0.7 and 5.0 dL/g as measured by ASTM D 2857-93, "Standard Practice for Dilute Solution Viscosity of Polymers". In addition, the polymer generally is predominantly amorphous. Useful poly-α-olefin polymers include, for example, $C_3$–$C_{18}$ poly(1-alkene) polymers, preferably $C_5$–$C_{12}$ α-olefins and copolymers of those with $C_3$ and more preferably $C_6$–$C_8$ and copolymers of those with $C_3$. Tackifying materials are typically resins that are miscible in the poly-α-olefin polymer. The total amount of tackifying resin in the poly-α-olefin polymer ranges between 0 to 150 parts by weight per 100 parts of the poly-α-olefin polymer depending on the specific application. Useful tackifying resins include resins derived by polymerization of $C_5$ to $C_9$ unsaturated hydrocarbon monomers, polyterpenes, synthetic polyterpenes and the like. Examples of such commercially available resins based on a $C_5$ olefin fraction of this type are WINGTACK™ 95 and WINGTACK™ 115 tackifying resins available from Goodyear Tire and Rubber Co. Other hydrocarbon resins include REGALREZ™ 1078 and REGALREZ™ 1126 available from Hercules Chemical Co., and ARKON™ P115 available from Arakawa Chemical Co. Other materials can be added for special purposes, including antioxidants, fillers, pigments, and radiation activated crosslinking agents.

Silicone pressure-sensitive adhesives comprise two major components, a polymer or gum, and a tackifying resin. The polymer is typically a high molecular weight polydimethylsiloxane or polydimethyldiphenylsiloxane, that contains residual silanol functionality (SiOH) on the ends of the polymer chain, or a block copolymer comprising polydiorganosiloxane soft segments and urea terminated hard segments. The tackifying resin is generally a three-dimensional silicate structure that is endcapped with trimethylsiloxy groups (OSiMe$_3$) and also contains some residual silanol functionality. Examples of tackifying resins include SR 545, from General Electric Co., Silicone Resins Division, Waterford, N.Y., and MQD-32-2 from Shin-Etsu Silicones of America, Inc., Torrance, Calif. Manufacture of typical silicone pressure-sensitive adhesives is described in U.S. Pat. No. 2,736,721(Dexter). Manufacture of silicone urea block copolymer pressure-sensitive adhesive is described in U.S. Pat. No. 5,214,119(Leir, et al). Other materials can be added for special purposes, including, pigments, plasticizers, and fillers. Fillers are typically used in amounts from 0 parts to 10 parts per 100 parts of silicone pressure-sensitive adhesive. Examples of fillers that can be used include zinc oxide, silica, carbon black, pigments, metal powders and calcium carbonate.

The second component of the pressure-sensitive adhesive composition of the present invention is a thermoplastic material or alternatively as either (a) a thermoplastic elastomeric material, (b) an elastomeric material with a tackifying resin, as previously described, or (c) an elastomeric material. The thermoplastic material component is typically a high polymer that can soften when exposed to heat and can return to the solid state when cooled to room temperature. Useful thermoplastic materials are fiber formers and are essentially immiscible in the pressure-sensitive adhesive component at the use temperature, although the thermoplastic may be miscible in the pressure-sensitive adhesive at melt processing temperatures. Typically, the thermoplastic material component comprises 2–70 weight percent at the pressure-sensitive adhesive composition, preferably 5–60 weight percent and more preferably 5–40 weight percent. Furthermore, the thermoplastic material component could be a single thermoplastic material or a mixture of several thermoplastic materials.

Thermoplastic materials useful in the present invention include, for example, polyolefins such as isotactic polypropylene, low density or linear low density polyethylene, medium density polyethylene, high density polyethylene, polybutylene, polyolefin copolymers or terpolymers, such as ethylene/propylene copolymer and blends thereof; ethylene-vinyl acetate copolymers such as ELVAX™ 260, available from DuPont Chemical Co., ethylene acrylic acid copolymers, ethylene methacrylic acid copolymers such as SURLYN™1702, available from DuPont Chemical Co., polymethylmethacrylate, polystyrene, ethylene vinyl alcohol, polyester, amorphous polyester, polyamides, fluorinated thermoplastics, such a polyvinylidene fluoride, polytetrafluoroethylene, fluorinated ethylene/propylene copolymers and fluorinated ethylene/propylene copolymers and halogenated thermoplastics, such as a chlorinated polyethylene. Any single thermoplastic can be blended with at least one pressure-sensitive adhesive. Alternatively, a blend of thermoplastic materials may be used, provided the resultant blend when melt mixed with at least one pressure-sensitive adhesive produces at least two distinct domains at the use temperature.

Thermoplastic elastomeric materials are typically materials that form at least two phases at 21° C., flow at a temperature greater than 50° C. and exhibit elastomeric properties. Thermoplastic elastomeric materials that are useful are further described in Ser. No. 08/578,010, filed Dec. 22, 1995 with a common assignee.

Elastomeric materials are typically materials that form one phase at 21° C., have a glass transition temperature less than about 0° C. and exhibit elastomeric properties. Tackifying resins may be added to facilitate blending of the pressure-sensitive component with the elastomeric material component. Elastomeric materials that are useful are further described in Ser. No. 08/577,603, filed Dec. 22, 1995 with a common assignee.

Preferably, each of the components has similar melt viscosity. The ability to form a finely dispersed morphology is related to a ratio of the shear viscosity of the components at melt mixing temperatures. Shear viscosity is determined using capillary rheometry at a shear rate approximating extrusion blending conditions, that is, 100s$^{-1}$ and 175° C. When a higher viscosity component is present as the minor component, the viscosity ratio of minor to major components is preferably less than about 20:1, more preferably less than about 10:1. When a lower viscosity material is present as the minor component, the viscosity ratio of minor to major components are preferably greater than about 1:20, more preferably greater than about 1:10. The melt viscosities of individual components may be altered by the addition of plasticizers tackifiers or solvents or by varying mixing temperatures.

It is also preferable that at least one of the components be easily extended during melt blending and coating operations to form a finely dispersed morphology with domains that are fibrillose to schistose, for example, forming sheets, ribbons, fibers, ellipsoids or the like, oriented in the down-web direction in the substantially continuous or co-continuous domain of the other polymeric material. Sufficient interfacial adhesion between the pressure-sensitive adhesive component and the thermoplastic material component preferably exists to withstand the shear and extensional deformation present during the forming step and to promote formation of a continuous film.

If none of the polymeric materials can be sufficiently dispersed during the melt blending, a pressure-sensitive adhesive coating may be produced that has gross discontinuities and is grainy in texture. Through use of suitably selected conditions of mixing, melt viscosity ratios, and shear/stretch conditions during extrusion, the thickness of the fibrillose to schistose domains can be made sufficiently thin that catastrophic delamination from the substantially continuous or co-continuous domain will not occur. Preferably, the thickness of the fibrillose to schistose domains is less than about 20 micrometers, more preferably less than about 10 micrometers, and most preferably less than about 1 micrometers.

In the present invention, the components are blended and coated using melt extrusion techniques. Mixing can be done by any method that results in a substantially homogeneous distribution of the components. The blend of components is prepared by melt mixing the components in the molten or softened state using devices that provide dispersive mixing, distributive mixing, or a combination of dispersive and distributive mixing. Both batch and continuous methods of blending may be used. Examples of batch methods include BRABENDER™ or BANBURY™ internal mixing, and roll milling. Examples of continuous methods include single screw extruding, twin screw extruding, disk extruding, reciprocating single screw extruding, and pin barrel single screw extruding. Continuous methods can include both distributive elements, pin mixing elements, and static mixing elements, and dispersive elements such as Maddock mixing elements or Saxton mixing elements.

After the mixing step, the softened or molten blend is formed into a coating of a blended pressure-sensitive adhesive that has a distinctive morphology. In the present invention the pressure-sensitive adhesive component forms a substantially continuous domain, while the thermoplastic material component forms a discontinuous domain that is fibrillose to schistose in nature by processes that involve either shear or extensional deformations or both.

Continuous forming methods include drawing the pressure-sensitive adhesive composition out of a film die and subsequently contacting a moving plastic web or other suitable substrate. A related continuous method involves extruding the pressure-sensitive adhesive composition and a coextruded backing material from a film die and subsequently cooling to form a pressure-sensitive adhesive tape. Other continuous forming methods involve directly contacting the pressure-sensitive adhesive blend to a rapidly moving plastic web or other suitable substrate. In this method, the pressure-sensitive adhesive blend can be applied to the moving web using a die having flexible die lips such as a reverse orifice coating die and other contact dies using rotating rods. After forming, the pressure-sensitive adhesive coatings are solidified by quenching using both direct methods, such as chill rolls or water baths, and indirect methods, such as air or gas impingement.

Either prior to or after a pressure-sensitive adhesive is coated onto a backing, the pressure-sensitive adhesive compositions of the invention may be cross-linked by treatment with radiation. Suitable radiation sources include ultraviolet and electron beam. When ultraviolet irradiation is used, photoinitiators are generally added to the adhesive blend. If present such photoinitiators are those that are known to those skilled in the article as being compatible or useful with specific pressure-sensitive adhesives.

Advantageously, blended pressure-sensitive adhesives of the present invention provide adhesives having one or more of the following properties. These properties are improvements over a pressure-sensitive adhesive prior to blended it with a thermoplastic material. These properties include:

(1) a peel adhesion greater than and shear strength similar to that of the pressure-sensitive adhesive component if used alone, (2) a shear strength greater than and peel adhesion similar to that of the pressure-sensitive adhesive component if used alone, (3) an anisotropic peel adhesion, (4) an anisotropic shear strength, and (5) a tensile stress in the down-web direction that is at least two times greater than the tensile stress in the cross-web direction for all elongations up to the break elongation.

Enhanced peel adhesions have been observed that are from 20% to 200% greater than those seen with the pressure-sensitive adhesive component alone without substantial decreases in shear strength. This appears to be due to the additional energy dissipation caused by limited interfacial delamination or void formation between the domains during peel. This is observed when the discontinuous domain is the thermoplastic material component. This will also depend on the type and amount of the component used. Generally enhanced peel adhesions occurs over a range of 5% to 20% thermoplastic component. For example, if an acrylic pressure-sensitive adhesive is used, thermoplastic material components that do not exhibit enhanced peel adhesion include, for example, polystyrene, polymethylmethacrylate and amorphous polyester. Likewise, thermoplastic materials that do exhibit enhanced peel adhesion include for example, linear low-density polyethylene. low-density polyethylene, and ethylene vinylacetate.

Shear strength, as measured by holding time, have been observed that are from 25% to 200% greater than those seen with the pressure-sensitive adhesive component alone without substantial decreases in peel adhesion. This appears to be due to the reinforcing nature of the thermoplastic material domains and has been observed over a range of thermoplastic material of 5% to 25%. Thermoplastic material types do not seem to be a controlling factor.

The anisotropic peel force is an unusual property wherein the force necessary to peel the PSA article from a surface to which it is adhered varies when measured along different axes. That is, the PSA article displays different adhesion when peeled from the surface in different directions. When a pressure-sensitive article is made by extruding the adhesive, the preferred orientation of the elastomer will generally be the "down-web direction" (or "DW"), that is, parallel to the extrusion coating line. The direction perpendicular to the extrusion coating line is generally referred to as the "cross-web direction" (or "CW"). Generally, the peel force in the parallel direction will be less than 90%, preferably less than 50%, and most preferably less than 10%, of the higher peel force (i.e., the peel force in the perpendicular direction). This effect is due to the down-web oriented fibrillous to schistose morphology of the discontinuous phase. When thermoplastic materials have a higher tensile strength, i.e., polystyrene, polymethylmethacrylate, amorphous polyester, and high density polyethylene, anisotropic peels are observed when the range of thermoplastic material is between 5 to 20%. When the thermoplastic material has a lower tensile strength, i.e., linear low density polyethylene, low density polyethylene, and ethylene vinyl acetate, the range is from 20% to 40%. It is believed that the anisotrdpic peel adhesion is due to the stiffening of the PSA composition by the thermoplastic material in the down-web direction.

Anisotropic shear strength is often observed when a pressure-sensitive adhesive of the invention exhibits anisotropic peel adhesion. In such cases, the direction of higher shear strength usually corresponds to the direction of lower peel adhesion. However, anisotropic shear strength can occur without the occurrence of a corresponding anisotropic peel adhesion. The shear strength in the low shear direction will be less than 80%, preferably less than 50%, and most preferably less than 10%, of the higher shear strength.

A tensile stress in the down-web direction has been observed that is at least two-times greater than the tensile stress in the cross-web direction for all elongations up to the break elongation. The tensile stress is influenced by the type of materials selected, their concentrations, the length to diameter ratio of the discontinuous domains and the break elongation of the thermoplastic material component. Tensile stresses have been observed ranging from 0.69 to 20.7 MPa (100 to 3000 psi) with constructions of the invention. By forming the fiber-like to schistose-like discontinuous domains in situ, finer thermoplastic fibrillous to schistose domains (less than 1 $\mu$m) can be formed compared to pressure-sensitive adhesive constructions composed of glass fiber placed in the pressure-sensitive adhesive. Generally, higher tensile stress properties are obtained with stiffer thermoplastic materials, such as polystyrene, polymethylmethacrylate, amorphous polyester and high density polyethylene. High down-web tensile stresses and smaller break elongations also afford pressure-sensitive adhesive compositions of the invention to have better dispensing properties when used, for example, as transfer adhesive tapes.

The compositions of the present invention, depending on specific formulation, can be used to make various pressure-sensitive articles utilizing the anisotropic properties of some formulations, pressure-sensitive adhesive tapes, pressure-sensitive adhesive transfer tapes, pressure-sensitive adhesive medical tapes, including for example transdermal drug delivering devices, or pressure-sensitive adhesive coatings directly onto desired articles. Alternatively, the various pressure-sensitive articles can utilize pressure-sensitive adhesive compositions comprising at least one pressure-sensitive adhesive component and at least one polymeric component that can be either (a) a thermoplastic elastomeric material, (b) an elastomeric material with a tackifying resin, as previously described, or (c) an elastomeric material without a tackifying resin.

The compositions of the present invention are also useful in medical applications including transdermal drug delivery devices. Such devices generally involve a controlled adhesion to skin. The adhesion should be enough for the application to stick initially and not increase over time to a point where skin may be damaged upon removal or decrease over time to a point where the devices may fall off the skin surface. Transdermal drug delivery devices are designed to deliver a therapeutically effective amount of drug through or to the skin of a patient. Transdermal drug delivery provides significant advantages; unlike injection, it is noninvasive; unlike oral administration, it avoids hepatic first pass metabolism, it minimizes gastrointestinal effects, and it provides stable blood levels.

A variety of transdermal drug delivery devices are known. Devices known to the art include matrices whereby the drug is placed within a non-adhesive polymeric material; reservoir devices in which the drug is placed in a liquid and delivered to the skin through a rate controlling membrane; drug-in-adhesive devices whereby the drug is placed within an adhesive polymer; and more complex multilaminate devices involving several distinct layers, e.g. layers for containing drug, for containing excipients, for controlling the rate of release of the drug and excipients, and for attaching the device to the skin.

All of the devices incorporate a drug formulation, an adhesive to maintain contact with the patient's skin, a release liner that protects the device during storage (and that is removed prior to the application of the device to the skin), and a backing that protects the device from external contamination while in use.

Figure 11:
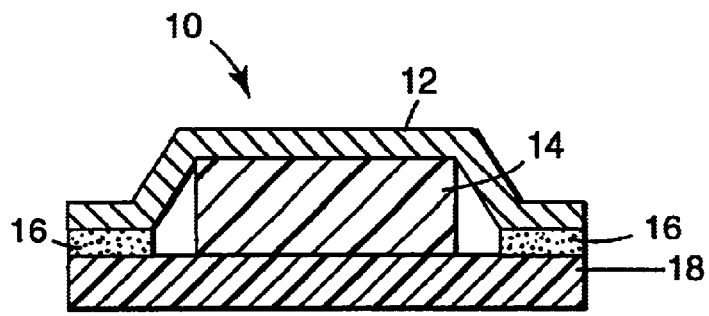
FIG. 11 is a cross-sectional view of a transdermal matrix device of the present invention.

A matrix device is shown in FIG. 11. Device 10 comprises a backing 12, a matrix 14 containing the drug and optionally excipients, a concentric adhesive layer 16 surrounding the matrix 14, and a release liner 18.

Figure 12:
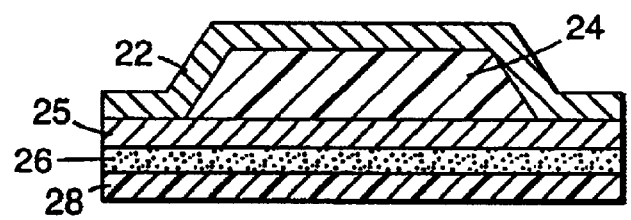
FIG. 12 is a cross-sectional view of a transdermal reservoir device of the present invention.

A reservoir device is shown in FIG. 12. Device 20 comprises a backing 22, a liquid formulation 24 containing the drug and optionally excipients, a membrane 25 for controlling the rate at which the drug and excipients are delivered to the skin, an adhesive layer 26, and a release liner 28. The adhesive layer may also be present as a concentric ring as depicted in connection with the matrix device (FIG. 11).

Figure 13:
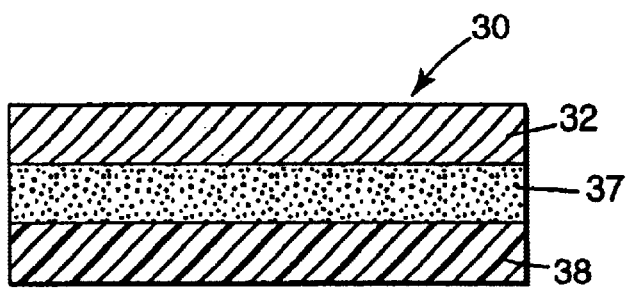
FIG. 13 is a cross-sectional view of a transdermal drug-in-adhesive device of the present invention.

A drug-in-adhesive device is shown in FIG. 13. Device 30 comprises a backing 32, an adhesive layer 37 containing drug and optionally excipients, and a release liner 38.

Figure 14:
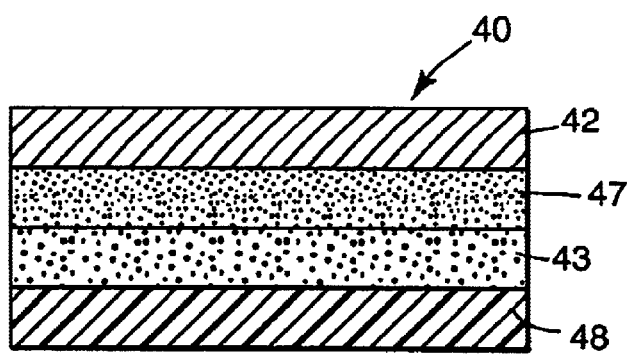
FIG. 14 is a cross-sectional view of a transdermal multilaminate device of the present invention.

A multilaminate device is shown in FIG. 14. Device 40 comprises a backing 42, an adhesive layer 47 containing drug and optionally excipients, a second adhesive layer 43 that controls the rate at which the drug and excipients are delivered to the skin, and a release liner 48.

Figure 15:
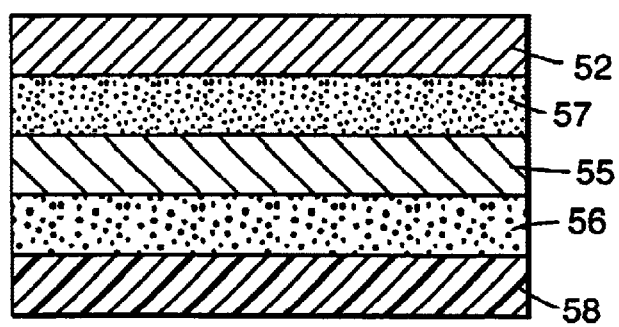
FIG. 15 is a cross-sectional view of an alternative embodiment of a transdermal multilaminate device of the present invention.

A second embodiment of a multilaminate device is shown in FIG. 15. Device 50 comprises a backing 52, an adhesive layer 57 containing drug and optionally excipients, a membrane 55, a second adhesive layer 56, and a release liner 58. The membrane may be selected to control the rate at which the drug and excipients are delivered to the skin or to provide physical stability to the device.

Skin adhesion is a critical requirement of any transdermal drug delivery system. Because drug delivery is directly proportional to the skin contact area, the device must establish and maintain sufficient skin adhesion until it is removed. Adhesives that are used in skin contacting layers will preferably exhibit the following properties: good initial skin adhesion, that is, tack; adequate adhesion during the wear period; clean release from the skin; and skin compatibility (nonirritating and nonsensitizing). It is important that these properties be maintained when the adhesive is exposed to the particular drug and excipients being used in a given device.

Adhesives used in layers that either contain drug and excipients or through which drug and excipients pass must also be compatible with the drug and excipients. Preferably the adhesives will not react chemically with the drug or excipients. In many instances, it is also preferable that the drug be dissolved in the adhesive rather than dispersed in it.

It will often be desirable or even necessary to customize the adhesive for a particular drug/excipient combination.

The transdermal delivery devices can be made in the form of an article such as a tape, a patch, a sheet, a dressing or any other form known to those skilled in the art. Generally the device will be in the form of a patch of a size suitable to deliver a preselected amount of the drug. Suitable release liners include those enumerated above in connection with the preparation of PSA tapes.

Anisotropic peel adhesion property enables pressure-sensitive adhesive articles of the invention (e.g., pressure-sensitive adhesive-coated tapes or sheets) to be advantageously used in graphic arts applications, (e.g., a premask tape, a prespace tape, a graphic art film, die-cut products, or dry transfer lettering, such as the graphic arts products described by Satas, supra, Chap. 32). The anisotropic PSA articles of this invention can also be used as a diaper fastening tape, a wall decoration film, or other constructions wherein differential peel is desirable.

As mentioned above, in one embodiment of the pressure-sensitive adhesive article of this invention, the type and concentration of the pressure-sensitive adhesive and thermoplastic material components are sufficient to impart anisotropic peel force to the article. An article having anisotropic peel force may be used as a graphics application tape (including both premask and prespace tapes), which is useful in graphic arts work. For example, die-cut graphics often take the form of such vinyl decals. Typically, the decal is formed by cutting it from a sheet of colored, adhesive-coated vinyl film which has been laminated to a release liner. The waste or weed is peeled away and then a graphics application tape is applied to the top of the die-cut decals to lift them from the release liner while keeping them in register. The decals are then transferred to the desired target substrate and the graphics application tape is peeled away. Such graphics application tapes need to be aggressive enough to reliably lift all of the components of the graphic (i.e., the decals in this example) from the release liner, but still should be easily removed after transferring the graphic to the target substrate and should not pull any of the graphic off the target. This is often a difficult balance to achieve. Using the pressure-sensitive adhesive tape of the present invention as the graphics application tape, one could pull in the high adhesion direction to remove the graphic from the liner, apply it to the target substrate, and then remove the graphics application tape by pulling in the low adhesion direction. Other graphics application tapes do not involve die-cut components but there would still be an advantage to having graphics application tapes with a very easy removal direction because the graphics can be very wide and difficult to pull off with conventional adhesives. When a conventional adhesive is formulated to have a low removal force, the ability to hold onto the graphic is impaired. The anisotropic pressure-sensitive adhesive tapes of the present invention can have high holding ability but still have a low removal force.

Another application for an anisotropic pressure-sensitive adhesive article of this invention is as a large area graphic or protective film that aggressively adheres to a surface that it is applied to but can be readily removed. Some useages of this article include, an advertising graphic on the side of a truck, a protective film for vehicle finishes during manufacture, transportation, storage, and a protective film for microreplicated surfaces used in graphic displays on optical screens.

Another application in which the anisotropic peeling properties of the invention can be used is in the manufacture of diaper fastening tape. The low peel force of such a tape in the machine direction would allow a large stock roll of the tape to be unwound for converting without the aid of a release material. In the process of converting the stock roll to individual tapes, the tape could be cut so the cross direction of the stock roll, which is the high adhesion direction, becomes the direction of peel on the finished diaper product.

Yet another application of the pressure-sensitive adhesive article would be in wall decoration films. One can produce a graphic wall decoration with the anisotropic pressure-sensitive adhesive article in such a way that the high adhesion direction is vertical or down the wall to prevent failure due to gravity, while the low adhesion direction is horizontal to provide an easy removal direction avoiding any damage to the wall.

Another use for an anisotropic pressure-sensitive adhesive article of the invention is in masking applications that use a maskant sheet or drape adhesively fixed to a substrate in order to mask a large area of the substrate. Maskant sheets or drapes are used in automotive painting or refinishing and in commercial and residential wall painting wherein a paper or plastic film is taped to the autobody part or the wall in order to prevent overspraying of a coating onto the area that is masked. If the maskant sheet is relatively long and heavy it will induce a constant peel force in the direction of the drape that may cause the tape to pull away from the substrate. The adhesive can be formulated to be more aggressive and overcome the stress induced by the weight of the drape, but the tape may then be difficult to remove completely from the substrate after the painting operation is completed. An anisotropic pressure-sensitive adhesive tape of the present invention that exhibits low peel force in the machine direction and high peel force in the cross direction is useful in such masking applications. The tape can be made to have high peel resistance or holding ability in the cross direction to overcome the peel stress induced by the weight of the drape, but have only a very low peel or removal force in the lengthwise direction to remove the tape without damage to the substrate.

Pressure-sensitive adhesive articles are made by applying the pressure-sensitive adhesive by well known hot melt coating processes. Any suitable substrates that can by used, including, but not limited to, for example, cloth and fiberglass cloth, metallized films and foils, polymeric films, nonwovens, paper and polymer coated paper, and foam backings. Polymer films include, but are not limited by, polyolefins such as polypropylene, polyethylene, low density polyethylene, linear low density polyethylene and high density polyethylene; polyesters such as polyethylene terephthalate; polycarbonates; cellulose acetates; polyimides such as KAPTON™. Nonwovens, generally made from randomly oriented fibers, include, but are not limited by, nylon, polypropylene, ethylene-vinyl acetate copolymer, polyurethane, rayon and the like. Foam backings include, but are not limited by acrylic, silicone, polyurethane, polyethylene, neoprene rubber, and polypropylene, and may be filled or unfilled. Backings that are layered, such as polyethylene-aluminum membrane composites, are also suitable.

In the case of pressure-sensitive tapes, these materials are typically applied by first making a tape construction which comprises a layer of the pressure-sensitive adhesive material coated on a backing. The exposed surface of the PSA coating may be subsequently applied to a surface from which it could be released later or directly to the desired substrate.

A transfer adhesive tape can be made by coating the composition between two liners both of which are coated with a release coating. The release liners often comprise a clear polymeric material such as polyolefin or polyester that is transparent to ultraviolet radiation. Preferably, each release liner is first coated with a release material for the pressure-sensitive adhesive utilized in the invention.

This invention is further illustrated by the following examples which are not intended to limit the scope of the invention. The following test methods were used to evaluate and characterize film surfaces produced in the examples.

EXAMPLES

This invention is further illustrated by the following examples which are not intended to limit the scope of the invention. In the examples, all parts, ratios and percentages are by weight unless otherwise indicated. The following test methods were used to characterize the pressure-sensitive adhesive compositions in the following examples:

Test Methods
Shear Viscosity

Shear viscosity was determined using a high pressure capillary rheometer (RHEOGRAPH 2001, available from Gottfert Co.) operated with a capillary die 30 mm long and 1 mm in diameter at a temperature of 175° C. unless otherwise noted. At a 100 s$^{-1}$ shear rate, the apparent viscosity was calculated from Poiseuille's equation and converted to true viscosity using the Weissenberg-Rabinovitch correction.

180° Peel Adhesion Test

Pressure-sensitive adhesive tape samples 1.25 cm wide and 15 cm long were tested for 180° peel adhesion to glass and/or smooth cast biaxially oriented polypropylene films. The samples were adhered to the test surfaces by rolling the tapes with a 2.1 kg (4.5 lb.) roller using 4 passes. After aging at controlled temperature and humidity conditions (approximately 22° C., 40% relative humidity) for approximately 1 hour, the tapes were tested using a Model 3M90 slip/peel tester, available from Instrumentors, Inc., in 180° geometry at 30.5 cm/min (12 in/min) peel rate, unless otherwise noted.

Shear Strength Test

Shear strength, as determined by holding time, was measured on pressure-sensitive adhesive tape samples at controlled temperature and humidity conditions (approximately 22° C., 40% relative humidity). A 25.4 mm×25.4 mm (1.0 in×1.0 in) section of the tape was adhered to a stainless steel sheet with a 2.1 kg (4.5 lb.) roller using 4 passes. A 1000 gram weight was hung from to the sample. The amount of time for the weight to drop was recorded. The test was stopped at 10,000 minutes.

Laser Light Scattering Test

Pressure-sensitive adhesive tape samples were tested for their light scattering characteristics. A helium neon laser operating at 632 nm wavelength and 3 mm spot size was directed normal to the plane of the adhesive tape. A shutter controlled the exposure time of the beam on the sample and the resulting light-scattering image was captured on Polaroid #55 film that was 120 mm behind the tape sample. The presence of the oriented fibrillous to schistose domains resulted in a smearing of the scattered light intensity into a fine or broad line oriented at 90 degrees from the fiber or down-web direction in the plane of the film. The absence of the dispersed domain or the presence of a spherically shaped dispersed domain resulted in a spherical or isotropic light scattering pattern.

Tensile Test

The tensile test was used to obtain stress-strain data for the various blended pressure-sensitive adhesive coatings. 2.54 cm (1.0 in) wide samples having thicknesses of 51 to 127 microns (2–5 mils) were tested using an INSTRON™ Model 1122 equipped with an INSTRON™ Series 9 software package at a cross-head speed of 102 cm/min (40 in/min). Samples were tested in both DW and CW directions.

Skin Adhesion Test

Skin adhesion testing was carried out by placing tape samples 2.5 cm wide by 5 cm long on the back of a human subject. Each tape was rolled down with one forward and one reverse pass using a 2 kg roller moved at a rate of about 30 cm/min. Adhesion to the skin was measured as the peel force required to remove the tape at 180° angle at a 15 cm/min rate of removal. Adhesion was measured immediately after initial application ($T_0$) and after 48 hours ($T_{48}$). Preferred skin adhesive generally exhibits a $T_0$ of between about 50 to 100 grams (1.9 to 3.8 N/dm) and a $T_{48}$ of between about 150 to 300 grams (5.8 to 11.5 N/dm). Results of 14 tests were averaged.

Skin Adhesion Lift Test

When the 48 hour skin adhesion test was performed, the tape sample was examined for the amount of area that was lifted (released) from the skin prior to removal of the tape and ratings were given as:

0 no visible lift
1 lift only at edges of tape
2 lift over 1% to 25% of test area
3 lift over 25% to 50% of test area
4 lift over 50% to 75% of test area
5 lift over 75% to 100% of test area Results of 14 tests were averaged. Preferred skin adhesives will generally exhibit an average rating below about 2.5.

Skin Adhesive Residue Test

When the 48 hour skin adhesion test was performed, the skin underlying the tape sample was visually inspected to determine the amount of adhesive residue on the skin surface and was rated as:

0 no visible residue
1 residue only at edges of tape
2 residue covering 1% to 25% of test area
3 residue covering 25% to 50% of test area
4 residue covering 50% to 75% of test area
5 residue covering 75% to 500% of test area Results of 14 tests were averaged. Preferred skin adhesives will generally exhibit an average rating below about 2.5.

Examples 1–17 and Comparative Examples C1

In Examples 1 and 2 a pressure-sensitive adhesive, acrylic component (95 weight percent isooctyl acrylate/5 weight percent acrylic acid, water emulsion polymerized, shear viscosity—150 Pa-s, prepared according to U.S. Pat. No. RE 24,906, (Ulrich) that is incorporated herein by reference, and dried), and a thermoplastic material component, ELVAX™ 210 (ethylene vinyl-acetate copolymer, shear viscosity 10 Pa-s, available from Dupont), were melt-blended in a 34 mm diameter fully intermeshing co-rotating twin-screw extruder (LEISTRITZ™ Model LSM34GL, available from Leistritz, Inc.). The thermoplastic material component was introduced into the feed throat of the extruder and the pressure-sensitive adhesive component was introduced in zone 4. The temperature was progressively increased from 38° C. to 177° C. (100° F. to 350° F.) from zone 1 to zone 4. The temperature of the remaining zones was maintained at 177° C. to 191° C. (350° F. to 375° F.). In Examples 1 and 2 the feed rates were adjusted to provide a ratio of pressure-sensitive adhesive component to thermoplastic material component of 95:5 and 85:15, respectively.

The twin-screw extruder was continuously discharged at a pressure of at least about 0.69 MPa (100 psi) into a 25.4 cm (10 inch) wide film die (ULTRAFLEX™ 40 die, Model 89-12939, available from Extrusion Dies, Inc.). The die was maintained at 177° C. to 191° C. (350° F. to 375° F.) and the die gap was 0.5 to 0.8 mm (20 to 30 mils). The blended adhesive composition was fed between a 51 μm (2 mil) thick biaxially oriented polyethylene terephthalate film and a release coated paper web at a rate of 6.4 kg/hr (14 lbs/hr). The film and the web were fed at a rate of 13.7 m/min (45 fpm) between chill rolls maintained at a temperature of 21° C. (70° F.) to form a pressure-sensitive adhesive tape with a pressure-sensitive adhesive composition layer thickness of about 64 microns (2.5 mils). Alternatively, some blended adhesive composition was fed between two release coated paper webs for further testing of the adhesive layer or subsequent transfer of the adhesive layer to a different substrate.

Examples 3, 4 and 5 were prepared in the same manner as Example 1 except that a different thermoplastic material component, ELVAX™ 240 (ethylene vinyl-acetate copolymer, shear viscosity—210 Pa-s), was added to the pressure-sensitive adhesive component at ratios of pressure-sensitive adhesive component to thermoplastic material component of 95:5, 85:15 and 70:30, respectively. Examples 6, 7 and 8 were prepared in the same manner as Examples 3, 4 and 5 respectively, except that a different thermoplastic material component, ELVAX™ 450 (ethylene vinyl-acetate copolymer, shear viscosity—470 Pa-s), was added to the pressure-sensitive adhesive component. Examples 9, 10, 11 and 12 were prepared in the same manner as Example 1 except that a different thermoplastic material component, ELVAX™ 260 (ethylene vinyl-acetate copolymer, shear viscosity—600 Pa-s), was added to the pressure-sensitive adhesive component at ratios of pressure-sensitive adhesive component to thermoplastic material component of 95:5, 85:15, 70:30 and 40:60, respectively. Examples 13, 14 and 15 were prepared in the same manner as Examples 3, 4 and 5, respectively, except that a different thermoplastic material component, ELVAX™ 660 (ethylene vinyl-acetate copolymer, shear viscosity—730 Pa-s) was added to the pressure-sensitive adhesive component. Examples 16 and 17 were prepared in the same manner as Examples 3 and 4 respectively, except that a different thermoplastic material component, SURLYN™ 1702 (ethylene-methacrylic acid copolymer, available from DuPont) was added to the pressure-sensitive adhesive component. Comparative Example C1 was prepared as in Example 1 except only the pressure-sensitive adhesive component, with no thermoplastic material component, was used to prepare the pressure-sensitive adhesive tape.

The viscosity ratio of the discontinuous to substantially continuous component and the thickness of adhesive on samples of each pressure-sensitive adhesive tape were determined and the 180° peel adhesion test on glass, the 180° peel adhesion test on biaxially oriented polypropylene (BOPP) and the shear strength were carried out in both the down-web (DW) and cross-web (CW) directions. The results are set forth in Table 1.

TABLE 1

| Example | Viscosity Ratio | Peel Adhesion Glass in DW/CW (N/dm) | Peel Adhesion BOPP in DW/CW (N/dm) | Shear Strength in DW/CW (min) |
|---|---|---|---|---|
| C1 | — | 39/48 | 33/32 | 230/190 |
| 1 | 1:15 | 43/42 | 24/32 | 210/230 |
| 2 | 1:15 | 62/68 | 27/30 | 230/390 |
| 3 | 1.4:1 | 46/49 | 27/28 | 240/270 |
| 4 | 1.4:1 | 70/65 | 17/31 | 370/420 |
| 5 | 1.4:1 | 70/61 | 22/29 | 170/650 |
| 6 | 3.1:1 | 49/54 | 29/33 | 220/150 |
| 7 | 3.1:1 | 11/65 | 28/40 | 300/240 |
| 8 | 3.1:1 | 1/40 | 7/33 | 190/130 |
| 9 | 4:1 | 47/50 | 24/33 | 210/290 |
| 10 | 4:1 | 46/52 | 25/36 | 220/310 |
| 11 | 4:1 | 20/59 | 20/23 | 640/760 |
| 12 | 4:1 | 5/11 | 2/3 | 120/40 |
| 13 | 4.9:1 | 39/49 | 30/35 | 270/200 |
| 14 | 4.9:1 | 29/58 | 25/30 | 200/220 |
| 15 | 4.9:1 | 6/47 | 10/21 | 190/160 |
| 16 | — | 28/38 | 27/15 | 150/220 |
| 17 | — | 56/44 | 23/29 | 430/340 |

Examples C1 through 17 exhibited the fibrillose to schistose morphology as determined by the laser light scattering test. As can be seen from the data in Table 1, the addition of the thermoplastic material components (ethylene vinyl-acetate copolymers and ethylene methacrylic acid copolymers) to the acrylic pressure-sensitive adhesive component increased the peel adhesion to glass and/or biaxially oriented polypropylene, and the shear strength of the control adhesive (C1) for Examples 1–4, 8, 9, 12 and 16. A concurrent increase of peel adhesion and shear strength is unusual since most rubber/resin pressure-sensitive adhesives have a trade-off between these two properties. The enhanced properties begin to be present at around 5% thermoplastic material component concentration. The peel adhesion enhancement is most pronounced for the examples containing ethylene vinyl-acetate copolymers. The shear strength was most pronounced for the examples containing ethylene methacrylic acid copolymers. Examples 5–7, 10–11 and 13–15 demonstrate that a significant anistropic peel adhesion can be obtained with cross-web peel adhesion significantly greater than the down-web peel adhesion.

Examples 18–22

Examples 18 and 19 and 20 were made according to Examples 3 and 4 and 5, respectively, except that a different thermoplastic material component, TENITE™ 1550P (a low-density polyethylene, shear viscosity—675 Pa-s, available from Eastman Kodak) was added to the pressure-sensitive adhesive component. Examples 21 and 22 were made according to Examples 1 and 2, respectively, except that a different thermoplastic material component, DOWLEX™ TM 2517 (a linear low-density polyethylene, shear viscosity—280 Pa-s, available from Dow Chemical) was added to the pressure-sensitive adhesive component.

The viscosity ratio of the discontinuous to substantially continuous component and the thickness of adhesive on samples of each pressure-sensitive adhesive tape were determined and the 180° peel adhesion test on glass, the 180° peel adhesion test on biaxially oriented polypropylene (BOPP) and the shear strength were carried out in both the down-web (DW) and cross-web (CW) directions. The results are set forth in Table 2 together with those of Comparative Example C1.

TABLE 2

| Example | Viscosity Ratio | Peel Adhesion Glass in DW/CW (N/dm) | Peel Adhesion BOPP in DW/CW (N/dm) | Shear Strength in DW/CW (min) |
|---|---|---|---|---|
| C1 | — | 36/43 | 30/29 | 230/190 |
| 18 | 4.5:1 | 47/45 | 29/33 | 200/210 |
| 19 | 4.5:1 | 37/59 | 24/38 | 180/80 |
| 20 | 4.5:1 | 9/23 | 5/20 | 10/50 |
| 21 | 1.9:1 | 24/49 | 31/38 | 270/350 |
| 22 | 1.9:1 | 91/82 | 35/42 | 340/320 |

Examples 18–22 exhibited the fibrillous morphology as determined by the light scattering test. As can be seen by the data in Table 2, the addition of the low-density and linear low-density polyethylene thermoplastic material component to the acrylic pressure-sensitive adhesive increased the peel adhesion to glass and/or biaxially oriented polypropylene and/or the shear strength of the control adhesive (C1) for Examples 19, 21 and 22. Examples 20–21 exhibited anisotropic behavior for all three properties.

Examples 23–29 and Comparative Examples C2

Examples 23–29 were made according to Example 1 except that a different pressure-sensitive adhesive layer thickness, different thermoplastic material components and various ratios of pressure-sensitive adhesive component to thermoplastic material component were used. In Examples 23–29 and Comparative Example C2, the pressure-sensitive adhesive layer thickness was approximately 90 μm. In Examples 23 and 24, the thermoplastic material component was FINA™ 3374x (a polypropylene, shear viscosity—700 Pa-s, available from Fina Oil and Chemical) was added to the pressure-sensitive adhesive component at ratios of 90:10 and 85:15, respectively. Examples 25 and 26 were made according to Examples 23 and 24, respectively, except that the thermoplastic material component was ESCORENE™ 3860 (a polypropylene, available from EXXON). Example 27 used DURAFLEX™ 0200 (a polybutylene, shear viscosity—682 Pa-s, available from Shell Chemical) and the ratio was 85:15.Examples 28 and 29 used PRIMACORE™ 1430 ethylene acrylic ester copolymer, shear viscosity—630 Pa-s, available from Dow Chemical) and the ratios were 92:8 and 87:13, respectively. Comparative Example C2 was made with only the pressure-sensitive adhesive component in the pressure-sensitive adhesive composition layer.

The viscosity ratio of the discontinuous to substantially continuous component of each pressure-sensitive adhesive tape were determined and the 180° peel adhesion test on glass, the 180° peel adhesion test on biaxially oriented polypropylene (BOPP) and the shear strength were carried out in both the down-web (DW) and cross-web (CW) directions. The results are set forth in Table 3 together with those of Comparative Example C2.

TABLE 3

| Example | Viscosity Ratio | Peel Adhesion Glass in DW/CW (N/dm) | Peel Adhesion BOPP in DW/CW (N/dm) | Shear Strength in DW/CW (min) |
|---|---|---|---|---|
| C2 | — | 52/50 | 39/37 | 100/130 |
| 23 | 4.7:1 | 64/59 | 39/38 | 110/180 |
| 24 | 4.7:1 | 56/56 | 30/34 | 150/240 |
| 25 | — | 69/74 | 50/40 | 80/150 |
| 26 | — | 62/58 | 40/46 | 250/280 |
| 27 | 4.5:1 | 68/66 | 36/42 | 130/180 |
| 28 | 4.2:1 | 68/68 | 34/32 | 120/150 |
| 29 | 4.2:1 | 62/55 | 33/40 | 110/150 |

Examples 23–29 exhibited the fibrillous morphology as determined by the light scattering test. As can be seen by the data in Table 3, the addition of various polypropylene thermoplastic material components to the acrylic pressure-sensitive adhesive increased the peel adhesion to glass and/or biaxially oriented polypropylene and/or the shear strength of the control adhesive (C2) for Examples 23–29. Examples 23–27 and 29 exhibited anisotropic behavior for one or more of the three properties.

Examples 30–33

Examples 30–33 were made according to Example 1 except that the temperature of zone 4 was 204° C. (400° F.), a different thermoplastic material components were used and the ratio of pressure-sensitive adhesive component to thermoplastic material component was 85:15.In Examples 30 and 31, the thermoplastic material component was Kodar™ 6763 (an amorphous polyester, shear viscosity—3150 Pa-s, available from Eastman Chemical Products) and Styron™ 615 (a polystyrene, shear viscosity—650 Pa-s, available from Dow Chemical), respectively. In Examples 32 and 33, the thermoplastic material component was Plexiglas™ VM100 (a polymethylmethacrylate, shear viscosity—1900 Pa-s, available from Ato Haas) and PETROTHENE™ 3150B (a high density polyethylene, shear viscosity—340 Pa-s, available from Quantum Chemical), respectively. The pressure-sensitive adhesive layer thickness was 64 μm (2.5 mils).

The viscosity ratio of the discontinuous to substantially continuous component the 180° peel adhesion test on glass, the 180° peel adhesion test on biaxially oriented polypropylene (BOPP) and the shear strength were carried out in both the down-web (DW) and cross-web (CW) directions. The results are set forth in Table 4 together with those of Comparative Example C1.

TABLE 4

| Example | Viscosity Ratio | Peel Adhesion Glass in DW/CW (N/dm) | Peel Adhesion BOPP in DW/CW (N/dm) | Shear Strength in DW/CW (min) |
|---|---|---|---|---|
| C1 | — | 39/48 | 33/32 | 230/190 |
| 30 | 21:1 | 21/50 | 33/45 | 70/90 |
| 31 | 4.3:1 | 9/46 | 3/40 | 90/140 |
| 32 | 13:1 | 39/39 | 41/38 | 60/90 |
| 33 | 2.3:1 | 69/64 | 43/40 | 90/140 |

Examples 30–33 exhibited the fibrillous morphology as determined by the light scattering test. As can be seen by the data in Table 4, the addition of various other thermoplastic material components to the acrylic pressure-sensitive adhesive resulted in anisotropic peel adhesion to glass and/or biaxially oriented polypropylene and/or anisotropic shear strength.

The pressure-sensitive adhesive layers of Examples 30–33 and Comparative Example C1 were also tested for tensile and elongation properties using the tensile and elongation test. FIG. 1 depicts the stress-stain curve for the down-web (DW) and cross-web (CW) directions of Example 31. The corresponding yield stresses for the down-web direction of Examples 30–33 were 3.5 Mpa (550 PSI), 20.7 Mpa (3000 PSI), 2.2 Mpa (317 PSI) and 6.3 Mpa (915 PSI), respectively. The cross-web direction of Examples 30–33 did not have a yield stress but were elastomeric in nature. The break elongation for Comparative Example C1 and Example 30–33 in the down-web direction was 1143%, 1125%, 650%, 962% and 911%, respectively. The break elongation for Comparative Example C1 and Examples 30–33 in the cross-web direction was 845%, 1638%, 1775%, 1970% and 1797%, respectively.

As the stiffer thermoplastic polymers were added to the acrylic pressure-sensitive adhesive, the down-web direction stress substantially increased, the down-web direction break elongation decreased while the cross-web direction break elongation increased. This leads to cleaner breaking of the pressure-sensitive adhesive when used alone as a transfer adhesive tape.

Examples 34–35 and Comparative Examples C3–C4

Examples 34–5 were made according to Example 33 except that a different pressure-sensitive adhesive component and a different thermoplastic material component were used. In Example 34 the pressure-sensitive adhesive was similar to that in Example 33 except 0.3 parts of acryloxybenzophenone, and the thermoplastic material was ELVAX™ 260. In Example 35, the pressure-sensitive adhesive was HRJ™ 4326 (2-ethyl hexyl acrylate, shear viscosity 10 Pa-s, available from Schenectedy International) and the thermoplastic material was ELVAX™ 240. Pressure-sensitive adhesive tapes of Comparative Examples C3 and C4 were made as in Examples 34 and 35, except they had no thermoplastic material component.

The viscosity ratio of the discontinuous to substantially continuous component of each pressure-sensitive adhesive tape were determined and the 180° peel adhesion test on glass, the 180° peel adhesion test on biaxially oriented polypropylene (BOPP) and the shear strength were carried out in both the down-web (DW) and cross-web (CW) directions. The results are set forth in Table 5.

TABLE 5

| Example | Viscosity Ratio | Peel Adhesion Glass in DW/CW (N/dm) | Peel Adhesion BOPP in DW/CW (N/dm) | Shear Strength in DW/CW (min) |
|---|---|---|---|---|
| C3 | — | 51/50 | 44/43 | 80/90 |
| 34 | 4:1 | 64/73 | 45/41 | 100/150 |
| C4 | — | 61/59 | 42/43 | 8580/6560 |
| 35 | 1:21 | 46/83 | 43/32 | 5640/5890 |

Examples 34–35 exhibited the fibrillous morphology as determined by the light scattering test. As can be seen by the data in Table 5, the addition of thermoplastic material components to the different acrylic pressure-sensitive adhesives resulted in anisotropic peel adhesion to glass for Example 35 and enhanced peel from glass for Example 34.

Examples 36–42 and Comparative Examples C5–C6

Examples 36–42 were made according to Example 1 except that a different pressure-sensitive adhesive and a different thermoplastic material component were used at various ratios of pressure-sensitive adhesive component to thermoplastic material component, and the thickness of the pressure-sensitive adhesive composition varied. In addition, the pressure-sensitive adhesive of some of the Examples contained a tackifying material. The pressure-sensitive adhesive used in Examples 36–42 and Comparative Examples C5–C6 was a suspension polymerized acrylic pressure-sensitive adhesive instead of the water emulsion polymerized adhesive used in Example 1. The suspension polymerized acrylic pressure-sensitive adhesive was prepared in accordance with U.S. Pat. No. 4,833,179 (Young et al.) in the following manner: A two liter split reactor equipped with condenser, thermowell, nitrogen inlet, stainless steel motor-driven agitator, and a heating mantle with temperature control was charged with 750 g deionized water, to which was added 2.5 g of zinc oxide and 0.75 g hydrophilic silica (CAB-O-SIL™ EH-5, available from Cabot Corp.) and was heated to 55° C. while purging with nitrogen until the zinc oxide and silica were thoroughly dispersed. At this point, a charge of 480 g isooctyl acrylate, 20 g methacrylic acid, 2.5 g initiator (VAZO™ 64, available from DuPont Co.) and 0.5 g isooctyl thioglycolate chain transfer agent were mixed together. The resulting solution with initiator and chain transfer agent was then added to the initial aqueous mixture while vigorous agitation (700 rpm) was maintained to obtain a good suspension. The reaction was continued with nitrogen purging for at least 6 hours, during which time the reaction was monitored to maintain a reaction temperature of less than 70° C. The resulting pressure-sensitive adhesive was collected and dried to at least 90% solids by weight. In Examples 36–39 the thermoplastic material component was Styron™ 615 and the ratio of the pressure-sensitive adhesive to thermoplastic material was 95:5, 90:10, 90:10 and 80:20, respectively. The pressure-sensitive adhesive tapes of Examples 40–42 were made according to Example 36, respectively, except the pressure-sensitive adhesive further contained an aliphatic/aromatic C9 tackifying material, ESCOREZ™ 2393 (available from EXXON) in a ratio of pressure-sensitive adhesive to tackifying material or 76:19, 76:19 and 64:16, respectively, and the thickness of the pressure-sensitive adhesive composition was approximately 46 μm, 30 μm and 33 μm, respectively. Comparative Examples C5 and C6 were made according to Example 36 except with only the pressure-sensitive adhesive component in the pressure-sensitive adhesive composition.

The thickness of adhesive on samples of each pressure-sensitive adhesive tape, the 180° peel adhesion test on glass, the 180° peel adhesion test on biaxially oriented polypropylene (BOPP) and the shear strength were carried out in both the down-web (DW) and cross-web (CW) directions. The results are set forth in Table 6.

TABLE 6

| Example | Thickness (μm) | Peel Adhesion Glass in DW/CW (N/dm) | Peel Adhesion BOPP in DW/CW (N/dm) | Shear Strength in DW/CW (min) |
|---|---|---|---|---|
| C5 | 46 | 46/42 | 24/26 | 120/200 |
| C6 | 33 | 45/40 | 23/23 | 180/210 |
| 36 | 46 | 55/52 | 6/24 | 340/460 |
| 37 | 46 | 22/56 | 6/29 | 290/390 |
| 38 | 28 | 21/54 | 2/24 | 240/390 |
| 39 | 46 | 3/51 | 2/19 | 410/600 |
| 40 | 46 | 75/75 | 11/17 | 370/420 |
| 41 | 30 | 58/71 | 10/14 | 440/700 |
| 42 | 33 | 44/63 | 36/62 | 360/430 |

Examples 36–42 exhibited the fibrillous morphology as determined by the laser light scattering test. As can be seen by the data in Table 6, the addition of thermoplastic material components to the different acrylic pressure-sensitive adhesives resulted in anisotropic peel adhesion to glass and/or biaxially oriented polypropylene and anisotropic shear strength. The pressure-sensitive adhesive properties were not significantly dependent on thickness over the range tested as seen by Comparative Examples C5 and C6. The addition of a tackifying material to the pressure-sensitive adhesive component shifted the peel adhesion values higher and decreased the anisotropic behavior.

Examples 43–46 and Comparative Examples C7–C9

A compounding and coating apparatus for making synthetic and natural rubber pressure-sensitive adhesives is described in U.S. Pat. No. 5,539,033, which is incorporated herein by reference. In Examples 43–44, a synthetic rubber, NATSYN™ 2210 (synthetic polyisoprene, shear viscosity—1500 Pa-s, available from Goodyear), a tackifier, EXCOREZ™ 1310LC and a plasticizer, mineral oil, and a thermoplastic material component, Styron™ 615 were melt blended in a 30 mm diameter fully intermeshing co-rotating twin screw extruder (Model ZSK 30, available from Werner-Pfleiderer, having a length to diameter ratio of 47:1). Both the elastomeric and thermoplastic polymers were fed into zone 1 (barrel 1) of the extruder. The tackifier was split-fed into zone 2 (barrel 6–10%) and zone 3 (barrel 8–90%). The plasticizer were fed into barrel 10. The temperature progressively increased from 60° C. to 204° C. from zone 1 to zone 5. The temperature of the remaining zones was maintained at 170° C. (350° F.). The screw speed was 200 revolutions per minute. The feed rates were adjusted to provide a pressure-sensitive adhesive component with a ratio of synthetic rubber to tackifier to plasticizer of 61:32:7 and a pressure-sensitive adhesive composition with a ratio of pressure-sensitive adhesive component to thermoplastic material component of 90:10 and 80:20 for Examples 43 and 44, respectively.

The blend was extruded onto 51 µm (2 mil) thick biaxially oriented polyethylene terephthalate film using a contact die with a rotating rod to form a pressure-sensitive adhesive tape having a pressure-sensitive adhesive layer thickness of 38 µm. The film was moving at 9 m/min (30 fpm). Example 45–46 were made according to Examples 43–44, respectively, except a natural rubber, (CV-60) was used in place of the synthetic rubber. Comparative Examples C7–C9 were made according to Examples 43 and 45, respectively, except no thermoplastic material component was added. Comparative Example C8 is Example 44 dissolved in toluene and coated onto 51 µM (2 mil) PET film.

The thickness of adhesive on samples of each pressure-sensitive adhesive tape were determined, and the 180° peel adhesion test on glass, the 180° peel adhesion test on biaxially oriented polypropylene (BOPP) and the shear strength were carried out in both the down-web (DW) and cross-web (CW) directions.

The results are set forth in Table 7.

TABLE 7

| Example | Peel Adhesion Glass in DW/CW (N/dm) | Peel Adhesion BOPP in DW/CW (N/dm) | Shear Strength in DW/CW (min) |
|---|---|---|---|
| C7 | 26/21 | 34/35 | 50/50 |
| 43 | 9/18 | 20/26 | 60/40 |

TABLE 7-continued

| Example | Peel Adhesion Glass in DW/CW (N/dm) | Peel Adhesion BOPP in DW/CW (N/dm) | Shear Strength in DW/CW (min) |
|---|---|---|---|
| 44 | 1/20 | 7/28 | 200/800 |
| C9 | 7/4 | 13/14 | 480/500 |
| 45 | 0/11 | 11/20 | 420/620 |
| 46 | 0/8 | 4/20 | 1300/1400 |
| C8 | 18/20 | — | 60/70 |

Figure 4:
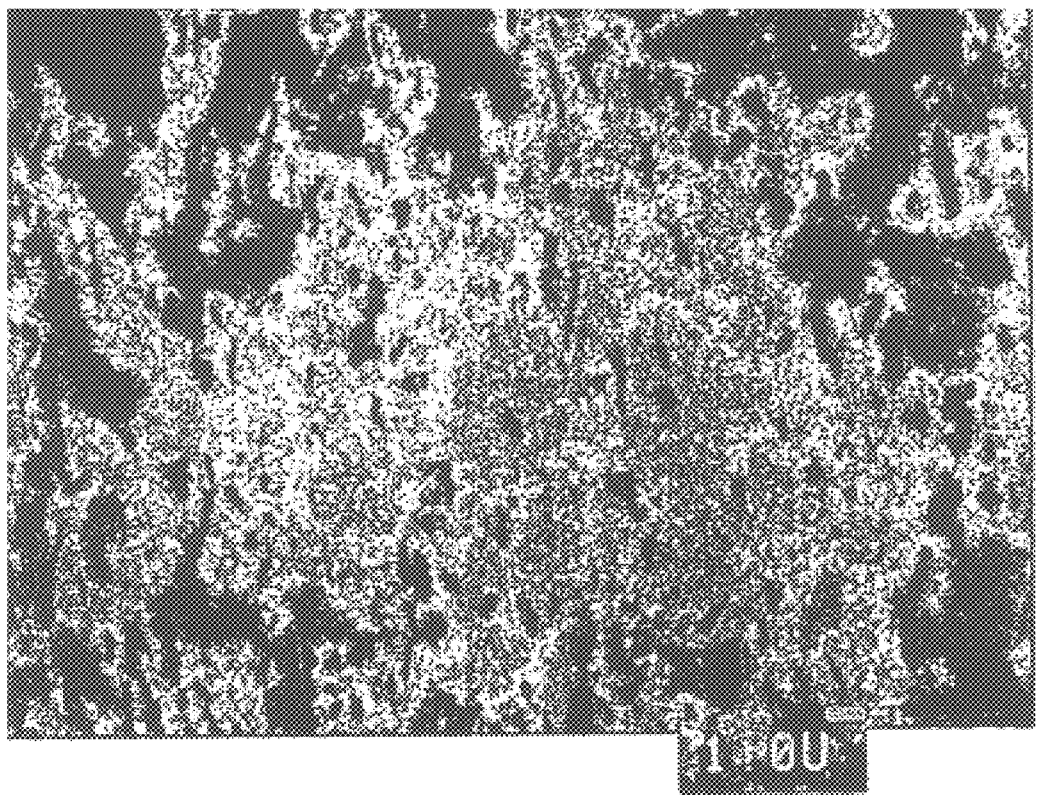
FIG. 4 is a cross-sectional view in the cross-web direction of the pressure-sensitive adhesive layer of Example 44 at 4000× using SEM.
Figure 5:
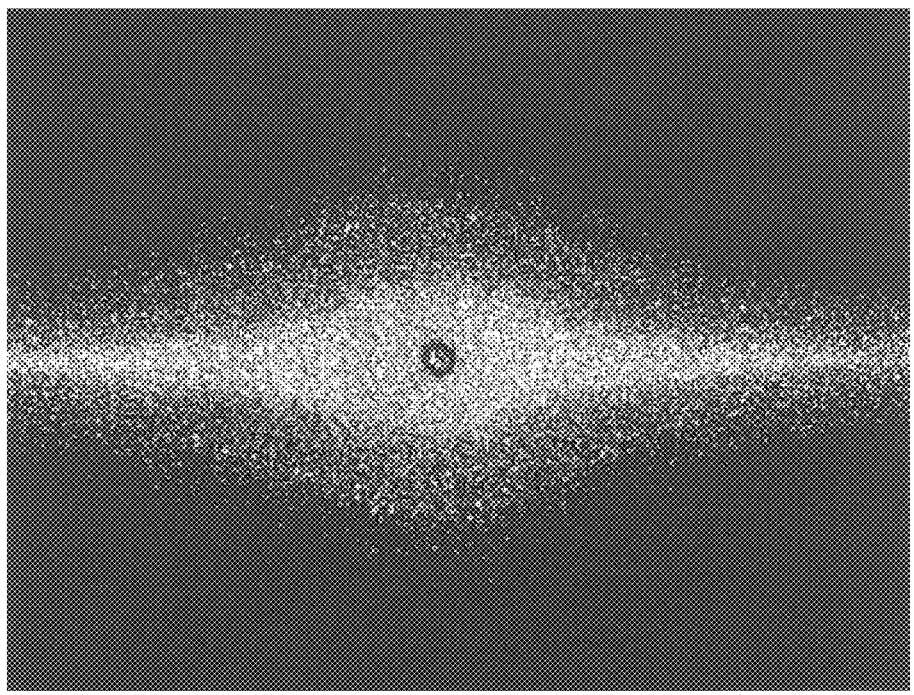
FIG. 5 is the light scattering pattern for the pressure-sensitive adhesive layer of Example 44 using the laser light scattering test.
Figure 6:
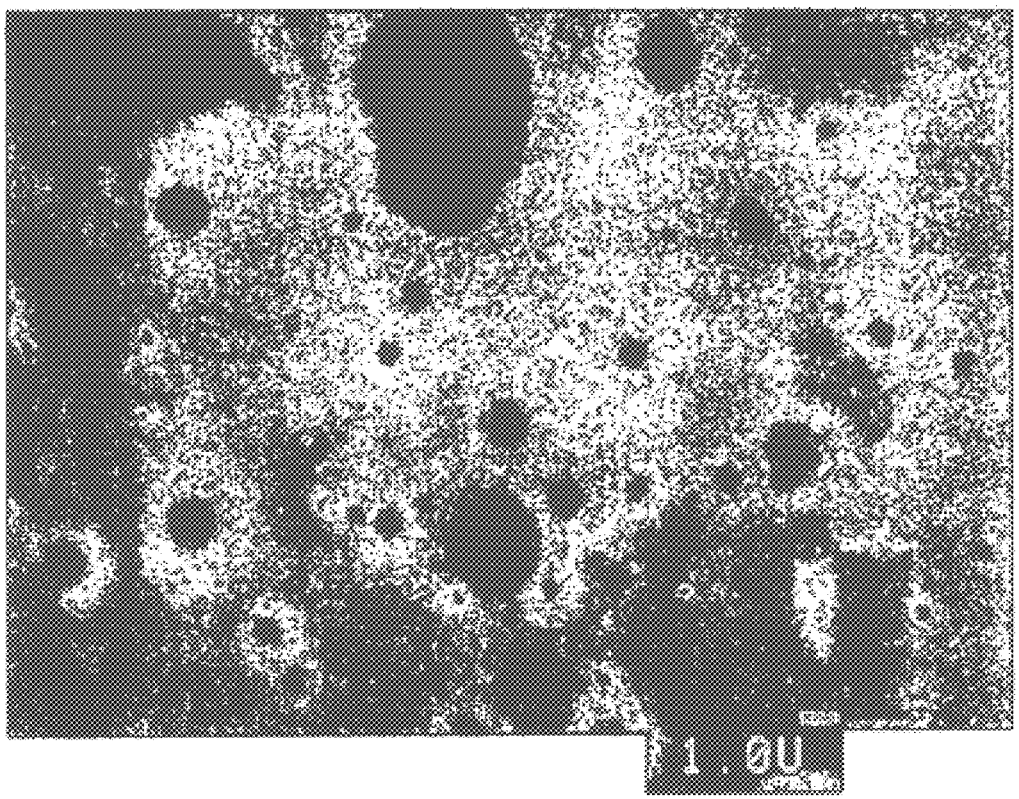
FIG. 6 is a cross-sectional view in the down-web direction of the pressure-sensitive adhesive layer of Comparative Example C8, at 4000× using SEM.
Figure 7:
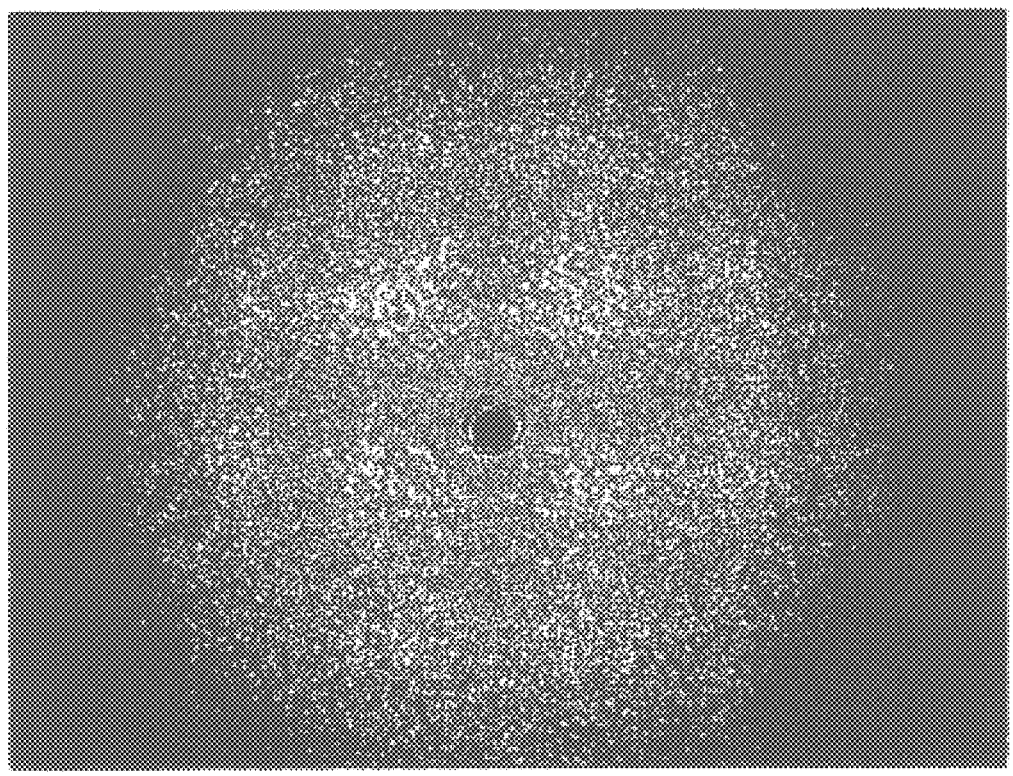
FIG. 7 is the light scattering pattern for the pressure-sensitive adhesive layer of Comparative Example C9, using the laser light scattering test.
Figure 8:
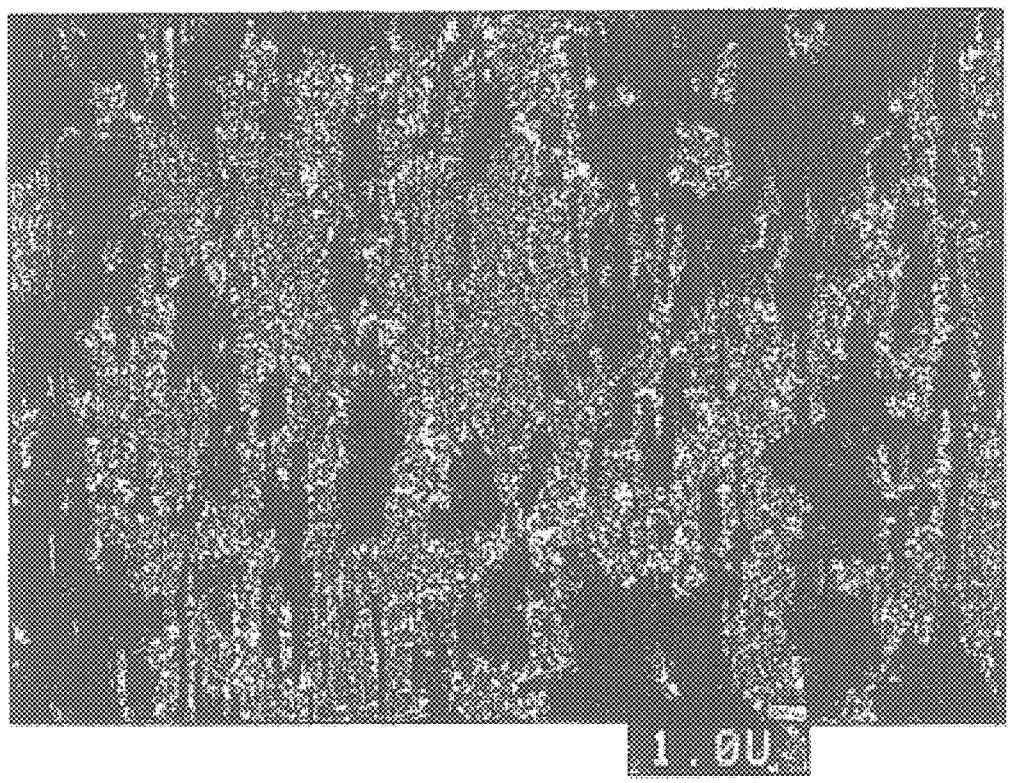
FIG. 8 is a cross-sectional view in the down-web direction of the pressure-sensitive adhesive layer of Example 46 at 4000× using SEM.
Figure 9:
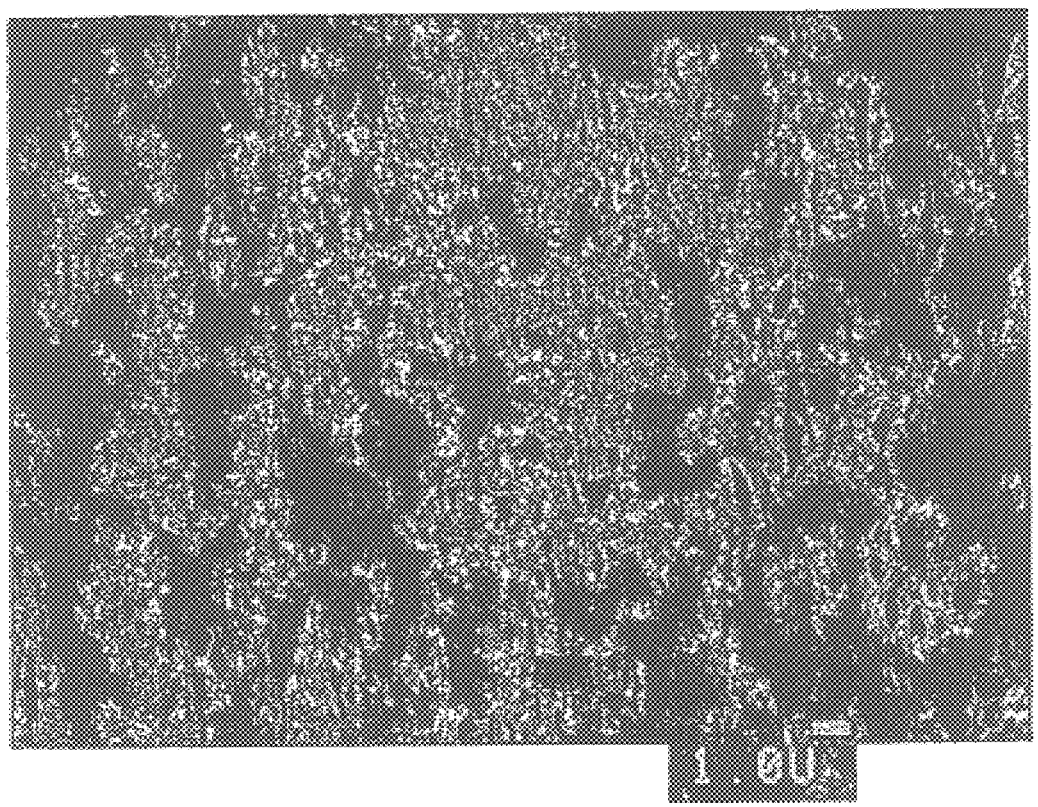
FIG. 9 is a cross-sectional view in the cross-web direction of the pressure-sensitive adhesive layer of Example 46 at 4000× using SEM.
Figure 10:
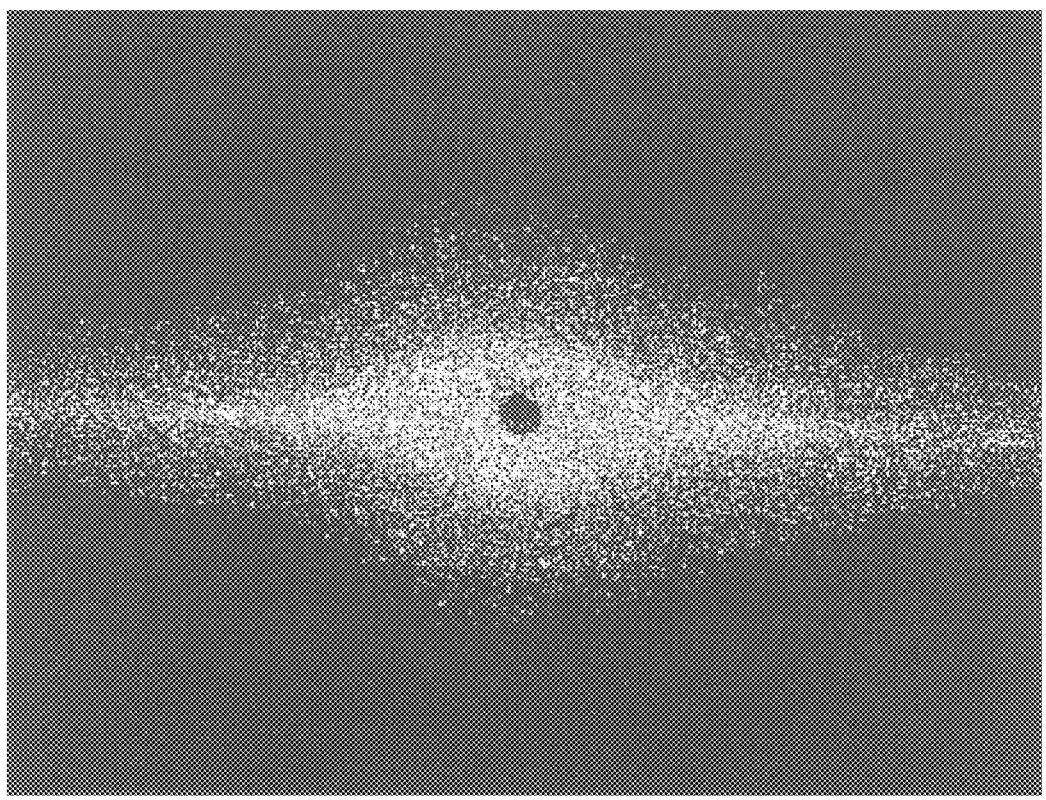
FIG. 10 is the light scattering pattern for the pressure-sensitive adhesive layer of Example 46 using the laser light scattering test.

Examples 43–46 exhibited the fibrillous morphology as determined by the laser light scattering test and is depicted in FIGS. 5 and 10 for Example 44 and Example 46, respectively. This was also confirmed by cryo-fracture SEM analysis of osmium tetroxide stained samples and is depicted in FIGS. 3–4, and 8–9 for Example 44 and Example 46, respectively. As can be seen by the data in Table 7, the addition of thermoplastic material components to either natural or synthetic rubber pressure-sensitive adhesives resulted in anisotropic peel adhesion to glass and biaxially oriented polypropylene. In addition, anisotropic shear strength was also observed. FIGS. 6 and 7 depict the spherical morphology for Comparative Example C8. This spherical morphology exhibits lower shear strength and isotropic peel adhesion as compared to the compositions of the invention.

Examples 47–50 and Comparative Examples C10–C11

Examples 47–50 and Comparative Examples C10–C11 were made according to Examples 43–46 and Comparative Examples C7 and C9, respectively, except they were subsequently exposed to electron beam radiation. Samples of each tape were subjected to electron beam radiation using an ELECTROCURTAIN™ Model CB-175 (available from Energy Sciences Incorporated, Wilmington, Mass.) at a 125 kV accelerating voltage. The irradiation was performed in an inert nitrogen atmosphere at a calculated dose of 4.0 Mrads.

The 180° peel adhesion test on glass, the 180° peel adhesion test on biaxially oriented polypropylene (BOPP) and the shear strength were carried out in both the down-web (DW) and cross-web (CW) directions. The results are set forth in Table 7.

TABLE 8

| Example | Peel Adhesion Glass in DW/CW (N/dm) | Peel Adhesion BOPP in DW/CW (N/dm) | Shear Strength in DW/CW (min) |
|---|---|---|---|
| C10 | 21/20 | 23/26 | 6580/3870 |
| 47 | 12/21 | 16/28 | 2370/2860 |
| 48 | 2/16 | 5/23 | 2040/4470 |
| C11 | 4/3 | 15/16 | 4060/4890 |
| 49 | 1/13 | 5/20 | 3390/4500 |
| 50 | 0/3 | 1/13 | 3170/3140 |

Examples 47–50 still exhibited the fibrillous morphology as determined by the laser light scattering test. This was also confirmed by cryo-fracture SEM analysis of osmium tetroxide stained samples. As can be seen by the data in Table 8, subsequent crosslinking generally raised shear strengths and decreased peel adhesions but did not significantly change the anisotropic properties.

Example 51 and Comparative Example C12

In Example 51 and Comparative Example C12, pressure-sensitive adhesive tapes were prepared as in Example 37 and Comparative Example C5, except the pressure-sensitive adhesive layer thickness was 58 µm and a different substrate was used. The substrate was a non-occlusive, i.e. breathable, woven backing which has an 180×48 plain weave acetate taffeta cloth, 75 denier fiber in the warp direction and 150 denier fiber in the weft direction, available from Milliken and Co., Spartanburg, Ga.

The pressure-sensitive adhesive tapes were tested in both the DW and CW direction for skin adhesion immediately after application, $T_0$, and after 48 hours, $T_{48}$, skin adhesion lift after 48 hours and skin adhesion residue after 48 hours.

The results are set forth in Table 9.

TABLE 9

|  | Example 51 | Comparative Example C12 |
|---|---|---|
| $T_0$ — DW (N/dm) | 25 | 81 |
| $T_0$ — CW (N/dm) | 43 | 74 |
| $T_{48}$ — DW (N/dm) | 149 | 265 |
| $T_{48}$ — CW (N/dm) | 199 | 264 |
| $T_{48}$ Lift — DW | 0.1 | 0.1 |
| $T_{48}$ Lift — CW | 0.1 | 0.4 |
| $T_{48}$ Residue — DW | 0.6 | 1.1 |
| $T_{48}$ Residue — CW | 0.6 | 1.1 |

As can be seen from the data in Table 9, the pressure-sensitive adhesive tapes of Example 51 had anisotropic peel performance from skin for the $T_0$:$T_{48}$ adhesion and can be controlled by appropriate blending of the acrylic adhesive component and the thermoplastic component. Thus the tape is easy to remove from skin when pulled in one direction but has good holding power.

Examples 52–57 and Comparative Examples C13–C14

The adhesives of the invention can control the rate of drug release from a multilayer transdermal drug delivery device as the procedure described below demonstrates. The rate control adhesives used in test patches of Examples 52–57 and Comparative Examples C13–C14 were made according to Examples 30, 32, 33, 34, 37, and 42 and Comparative Examples C13–C14, respectively, except each adhesive was applied to a release paper.

Each test patch consisted of 4 layers: a backing, a first adhesive layer containing drug, a second adhesive layer to provide rate control, and a release liner. Acrylate adhesive copolymer (57.5/39/3.5 w/w/w isooctyl acrylate/2-hydroxyethyl acrylate/ELVACITE™ (ICI Acrylics) 1020 polymethylmethacrylate macromonomer 50% solids in ethyl acetate) and phenobarbitol were combined then mixed to provide a homogeneous coating formulation. The formulation was coated onto a backing (1109 SCOTCHPAK™ tan, polyester film laminate, available from 3M Company) then dried at 43° C. for 15 minutes. The resulting coating contained 5 percent by weight of phenobarbital and had a thickness of 5 mils (127 µm). The exposed surface was laminated to a layer of rate control adhesive of the invention carried on a release liner. Test patches (round, 5 cm²) were die cut from the resulting laminate.

To prevent release of the drug from the periphery of the patch, each test patch was concentrically aligned with an adhesive overlay. An adhesive overlay (round, 25 cm², 1, mil (25 µm) layer of polyisobutylene coated onto a backing) was laminated to the backing of the test patch such that the patch and the overlay were concentrically aligned. The release liner was removed from the test patch. A ring-shaped overlay (25 cm², with an inner diameter of 22 mm, 1 mil (25 µm) layer of polyisobutylene coated onto a backing) was centered over the test patch/overlay laminate, then the adhesive surfaces were laminated together to provide a seal around the periphery of the test patch. The release liner was placed back on the test patch, then the entire assembly was die cut (round 12.5 cm²) so that the test patch was centered. The assembly was heat sealed in a foil pouch and allowed to equilibrate for 8 days.

The assembly was then removed from the pouch and affixed to one end of a glass plate with double coated tape, so the backing of the assembly was in direct contact with the double coated tape. The release liner was removed from the test patch. The glass slide was suspended in a 120 ml tall form glass jar equipped with a magnetic stirrer. A release solution was prepared by combining 6 L of HPLC grade water; 2.2835 g of sodium phosphate, monobasic monohydrate; 9.7538 g of sodium phosphate, dibasic heptahydrate; and 46.4502 g sodium chloride. A 100 ml portion of 32° C. release solution was added to the jar. The test patch was completely submerged in the release solution. The jar was capped, then placed in a temperature controlled chamber at 32° C. The release solution was stirred throughout the experiment.

At specified time points (1 hr, 6.5 hr, 24 hr, 72 hr, 168 hr and 336 hr), the cap was removed and a 1.0 mL sample of release solution was removed and placed in a HPLC sample vial. The phenobarbitol content of the sample was quantitated using reverse-phase high performance liquid chromatography (Waters LC1 Module Plus; column: 15 cm×4.6 mm inner diameter Supelcosil LC-ABZ, 5 µm particle size; mobile phase: 75% 25 mM potassium phosphate monobasic buffer/25% acetonitrile v/v; flow rate: 2.0, ml/min; detector: uv, 254 , nm at 0.005 AUFS; run time: 10 minutes; injection volume 20 µL).

The percent released was obtained using the following equation:

$$R_i = \frac{\left[C_i \times (100 - (I-1))] + \sum_{a=1}^{i} C_{a-1}\right]}{(T.C. \times S.A.)} \times 100$$

where:

$R_i$=percent of phenobarbitol released from the sample a time point "i"

i=sequential number of time point (values: 1, 2, 3 . . . n)

$C_i$=sample concentration (µg/mL) HPLC analysis at time point I $C_0$=0

T.C.=theoretical phenobarbitol content in µg/cm²

S.A.=surface area of test patch in cm²

The table below shows the thickness of the rate control adhesive and the cumulative percent released at each time point. Each value is the average of determinations for four separate test patches.

TABLE 10

| | | Release Rate of Phenobarbitol in Percent | | | | | |
|---|---|---|---|---|---|---|---|
| Example | Thickness | 1 hr | 6.5 hr | 24 hr | 72 hr | 168 hr | 336 hr |
| 52 | 63.5 | 3 | 13 | 36 | 77 | 96 | 100 |
| 53 | 63.5 | 4 | 12 | 36 | 76 | 95 | 100 |

TABLE 10-continued

Release Rate of Phenobarbitol in Percent

| Example | Thickness | 1 hr | 6.5 hr | 24 hr | 72 hr | 168 hr | 336 hr |
|---------|-----------|------|--------|-------|-------|--------|--------|
| 54 | 63.5 | 3 | 9 | 29 | 66 | 91 | 99 |
| 55 | 127 | 3 | 9 | 21 | 51 | 83 | 97 |
| C13 | 63.5 | 4 | 15 | 41 | 81 | 97 | 100 |
| 56 | 45.7 | 3 | 9 | 29 | 63 | 90 | 99 |
| 57 | 45.7 | 1 | 5 | 13 | 33 | 61 | 84 |
| C14 | 45.7 | 4 | 11 | 36 | 73 | 93 | 100 |

The rate of diffusion of a drug can be varied by the addition of another substantially immiscible thermoplastic material component to a pressure-sensitive adhesive where the minor component forms discrete domains that have a fibrillous to schistose morphology. This augments the differential adsorption and desorption effects of two polymeric domains with a torturous path caused during the formation of the rate controlling adhesive layer.

Example 58 and Comparative Examples C15–C17

The adhesives of the invention that contain thermoplastic elastomeric components can control the rate of drug release from a multilayer transdermal drug selivery device as the procedure below demonstrates. In Example 58, the water suspension polymerizd acrylic pressure-sensitive adhesive component described in Example 36 was melt blended with a thermoplastic elastomeric adhesive component (prepared by blending 50 parts thermoplastic elastomeric block copolymer KRATON™ D1107P, 1 part antioxidant IRGANOX™ 1010 and 50 parts tackifying resin ESCOREZ™ 1310LC) in a corotating twin screw extruder, Model ZSK 30, having 30 mm diameter barrel and a length to diameter ratio of 37:1 with the acrylic adhesive to thermoplastic elastomer adhesive ratio being 50:50, respectively. The thermoplastic elastomer block copolymer was fed into zone 1, the tackifying resin in zone 2 and the acrylic pressure-sensitive adhesive in zone 3. Temperatures were maintained between 249° C. and 165° C. The resulting pressure-sensitive adhesive composition was applied to release papers such that the adhesive layer was 51 μm thick.

In Comparative Example C15, the pressure-sensitive adhesive was prepared using only the acrylic adhesive of Example 58. In Comparative Example C16, the pressure-sensitive adhesive was prepared as follows. Acrylate adhesive in example 36 was dissolved in a 90/10 heptane/isopropyl alcohol mixture at 20% solids. The thermoplastic elastomer Kraton™ 1107 and tackifier ESCOREZ™ 1310LC at a 50/50 mix were dissolved in toluene at 50% solids.

The 50/50 ratio of acrylate/tacified thermoplastic elastomer was prepared by combining the appropriate amounts of acrylate adhesive and kraton adhesive blend.

The pressure-sensitive composition in solvent was knife coated and dried. The dried coating thickness was 51 μm (2 mil). The drying conditions were 5 minutes at 43° C. (110° F.), 2 minutes at 85° C. (185° F) and 2 minutes at 107° (225° F.).

In Comparative Example C17, the pressure-sensitive adhesive was prepared using only the tackified thermoplastic elastomer component of Example 58.

Each test patch consisted of 4 layers: a backing, a first adhesive layer containing drug, a second adhesive layer to provide rate control, and a release liner. Acrylate adhesive copolymer (59/39/2 w/w/w isooctyl acrylate/2-hydroxyethyl acrylate/ELVACITE™ (ICI Acrylics) 1020 polymethylmethacrylate macromonomer 51.9% solids in 95/5 ethyl acetate/isopropanol) and phenobarbital were combined then mixed to provide a homogeneous coating formulation. The formulation was coated onto a backing (1109 SCOTCHPAK™ tan, polyester film laminate, available from 3M Company) then dried at 43° C. for 15 minutes. The resulting coating contained 8 percent by weight of phenobarbital and had a thickness of 15 mils (382 μm). The exposed surface was laminated to a 2 mil (51 μm) layer of rate control adhesive carried on a release liner. Test patches (round, 5 cm$^2$) were die cut from the resulting laminate.

To prevent release of the drug from the edge of the patch, each test patch was fitted with an adhesive overlay. An adhesive overlay (round, 25 cm$^2$, 1 mil (25 μm) layer of polyisobutylene coated onto a backing) was laminated to the backing of the test patch such that the patch and the overlay were concentrically aligned. The release liner was removed from the test patch. A ring-shaped overlay (25 cm$^2$, with an inner diameter of 22 mm, 1 mil (25 μm) layer of polyisobutylene coated onto a backing) was centered over the test patch/overlay laminate, then the adhesive surfaces were laminated together to provide a seal around the periphery of the test patch. The release liner was placed back on the test patch, then the entire assembly was die cut (round 12.5 cm$^2$) so that the test patch was centered. The assembly was heat sealed in a foil pouch and allowed to equilibrate for 8 days.

The assembly was then removed from the pouch and affixed to one end of a glass plate with double coated tape, so that backing of the assembly was in direct contact with the double coated tape. The release liner was removed from the test patch. The glass slide was suspended in a 120 ml tall form glass jar equipped with a magnetic stirrer. A release solution was prepared by combining 61 of HPLC grade water; 2.2835 g of sodium phosphate, monobasic monohydrate; 9.7538 g of sodium phosphate, dibasic heptahydrate; and 46.4502 g sodium chloride. A 100 mL potion of 32° C. release solution was added to the jar. The test patch was completely submerged in the release solution. The jar was capped, then placed in a temperature controlled chamber at 32° C. The release solution was stirred throughout the experiment.

At specified time points (1 hr, 4 hr, 8 hr, 24 hr, 97.5 hr, 168 hr, 264 hr and 336 hr), the cap was removed and a 1.0 ml sample of release solution was removed and placed in a HPLC sample vial. The phenobarbital content of the sample was quantitated using reverse-phase high performance liquid chromatography (Waters LC1 Module Plus; column: 15 cm×4.6, mm inner diameter Supelcosil LC-ABZ, 5 μm particle size; mobile phase: 75% 25 mM potassium phosphate monobasic buffer/25% acetonitrile v/v; flow rate: 2.0 ml/min; detector: uv, 254 nm at 0.005 AUFS; run time: 10 minutes, injection volume 20 μl).

The percent released was obtained using the following equation:

$$R_i = \frac{\left[ C_i \times (100 - (I-1)) + \sum_{a=1}^{i} C_{a-1} \right]}{(T.C. \times S.A.)} \times 100$$

where:

$R_i$=percent of phenobarbital released from the sample a time point "i"

i=sequential number of time point (values: 1, 2, 3 . . . n)

$C_i$=sample concentration (μg/ml) HPLC analysis at time point I $C_0 = 0$

T.C.=theoretical phenobarbital content in $\mu g/cm^2$

S.A.=surface area of test patch in $cm^2$

The table below shows the identity of the adhesive used in the rate control layer and the cumulative percent released at each time point. Each value is the average of determinations for four separate test patches.

TABLE 11

Release Rate of Phenobarbitol in Percent

| Example | 1 hr | 8 hr | 24 hr | 49 hr | 97.5 hr | 168 hr | 264 hr | 336 hr |
|---------|------|------|-------|-------|---------|--------|--------|--------|
| C15     | 1    | 3    | 9     | 16    | 27      | 41     | 56     | 64     |
| 58      | 0    | 0    | 1     | 1     | 2       | 4      | 6      | 7      |
| C16     | 0    | 1    | 2     | 3     | 6       | 11     | 18     | 22     |
| C17     | 0    | 0    | 0     | 0     | 1       | 1      | 2      | 2      |

The rate of diffusion of a drug can be varied by the addition of another substantially immiscible thermoplastic material component to a pressure-sensitive adhesive where the minor component forms discrete domains that have a fibrillous to schistose morphology. As seen by comparing Example 58 to Comparative Example C16, the fibrillous to schistose morphology augments the differential adsorption and desorption effects of two polymeric domains with a torturous path caused during the formation of the rate controlling adhesive layer.

Example 60

In Example 60, a pressure-sensitive adhesive component as described in Example 36 was melt-blended in a 30 mm diameter fully intermeshing co-rotating twin screw extruder (Model ZSK-30, available from Werner & Pfleiderer Corp., Ramsey, N.J., having a length to diameter ratio of 36:1) with a process similar to that described in Example 19 of U.S. Pat. No. 5,539,033. The screw configuration used was the same as shown in FIG. 4 of U.S. Pat. No. 5,539,033. The elastomeric polymer, NATSYN™ 2210 was added in zone 1. The acrylic pressure-sensitive adhesive was added in zone 9. The elastomer to acrylic pressure-sensitive adhesive ratio was 50:50. The screw speed was 475 rpm. Air was injected into zone 3 and the temperature was maintained at 133° C. to reduce the molecular weight of the elastomer in order to make it more hot melt processable. The die temperature was 154° C. The pressure-sensitive adhesive was applied as a 42 $\mu m$ thick layer onto a 30 $\mu m$ thick polyethylene terephthalate film moving at 9.1 m/min. The pressure-sensitive adhesive layer was essentially non-grainy, tacky to the touch, and exhibited the fibrillous morphology as determined by the light scattering test.

The various modifications and alterations of this invention will be apparent to those skilled in the art without departing from the scope and spirit of this invention and this invention should not be restricted to that set forth herein for illustrative purposes only.

What is claimed is:

1. A pressure-sensitive adhesive layer comprising a blend of at least one pressure-sensitive adhesive component and at least one thermoplastic, elastomeric, tackified elastomeric, or thermoplastic elastomeric material component being immiscible with the pressure-sensitive adhesive component at room temperature, said layer having an anisotropic morphology comprising two axes perpendicular to each other, both parallel to the main surface layer, said axes comprising a longitudinal axis in the down-web direction and a transverse axis in the cross-web direction, said morphology further comprising at least two distinct domains, a first substantially continuous domain comprising the at least one pressure sensitive adhesive component and a second domain comprising the at least one thermoplastic, elastomeric, tackified elastomeric, or thermoplastic elastomeric material component being fibrillose to schistose in nature and oriented along the down-web direction.

2. The pressure-sensitive adhesive layer of claim 1 having at least one pressure-sensitive adhesive property from the group consisting of (a) a peel adhesion greater than and shear strength similar to that of the pressure-sensitive adhesive component if used alone, (2) a shear strength greater than and peel adhesion similar to that of the pressure-sensitive adhesive component if used alone, (3) an anisotropic peel adhesion, (4) an anisotropic shear strength and (5) a tensile stress in the down-web direction that is at least two times greater than the tensile stress in the cross-web direction for all elongations up to the break elongation.

3. The pressure-sensitive adhesive layer of claim 1 wherein the pressure-sensitive adhesive component is selected from the group consisting of acrylic, styrene block copolymer, natural rubber, synthetic rubber, silicone urea polymer, polyurethane, polyvinylmethylether and blends thereof.

4. The pressure-sensitive adhesive layer of claim 3 wherein the pressure-sensitive adhesive component is acrylic.

5. The pressure-sensitive adhesive layer of claim 4 wherein the acrylic pressure-sensitive adhesive component comprises a polymer of a $C_3$–$C_{12}$ alkyl ester.

6. The pressure-sensitive adhesive layer of claim 5 wherein the acrylic pressure-sensitive adhesive component comprises a polymer of isooctyl acrylate, 2-ethyl-hexyl acrylate or n-butyl acrylate.

7. The pressure-sensitive adhesive layer of claim 4 wherein the acrylic pressure-sensitive adhesive component further comprises a polar component.

8. The pressure-sensitive adhesive layer of claim 7 wherein the polar component comprises acrylic acid, methacrylic acid, ethylene vinyl acetate, N-vinyl pyrrolidone and styrene macromer.

9. The pressure-sensitive adhesive layer of claim 8 wherein the acrylic pressure-sensitive adhesive component comprises about 100 to 80 weight percent alkyl ester component and up to about 20 weight percent polar component.

10. The pressure-sensitive adhesive layer of claim 1 wherein the pressure-sensitive adhesive component is silicone urea.

11. The pressure-sensitive adhesive layer of claim 1 wherein the pressure-sensitive adhesive component is poly-alpha-olefin.

12. The pressure-sensitive adhesive layer of claim 1 wherein the pressure-sensitive adhesive component is natural rubber or synthetic rubber.

13. The pressure-sensitive adhesive layer of claim 1 wherein the thermoplastic elastomeric materials comprise linear, radial, star, tapered or branched copolymers.

14. The pressure-sensitive adhesive layer of claim 1 wherein the thermoplastic elastomeric material component is selected from the group consisting of linear, radial, star and tapered styrene-isoprene block copolymers, linear styrene-(ethylene-butylene) block copolymers, linear styrene-(ethylene-propylene) block copolymers, styrene-isoprene-styrene block copolymers, star styrene-butadiene block copolymers, polyetheresters, and poly-alpha-olefins.

15. The pressure-sensitive adhesive layer of claim 1 wherein the thermoplastic material component is selected from the group consisting of ethylene-vinyl acetate, polyolefin, polystyrene, amorphous polyester, polymethyl methacrylate, isotactic polypropylene, linear low density polyethylene, low density polyethylene, high density polyethylene, polybutylene, and nylon.

16. The pressure-sensitive adhesive layer of claim 1 wherein the elastomeric material component is selected from the group consisting of natural rubbers, butyl rubbers, synthetic polyisoprenes, ethylene-propylenes, polybutadienes, polyisobutylenes, and styrene-butadiene random copolymer rubbers.

17. The pressure-sensitive adhesive layer of claim 1 further comprising a tackifier.

18. The pressure-sensitive adhesive layer of claim 16 further comprising a tackifier selected from the group consisting of rosins, synthetic hydrocarbon resins, terpene resins, and liquid rubbers.

19. The pressure-sensitive adhesive layer of claim 1 comprising a thermoplastic elastomeric material component and further comprising a tackifying resin, said tackifying resin optionally comprising up to 200 weight percent based on the weight percent of thermoplastic elastomeric material.

20. The pressure-sensitive adhesive layer of claim 1 wherein the layer comprises 40 to 95 weight percent pressure-sensitive adhesive component and 5 to 60 weight percent thermoplastic material component.

21. The pressure-sensitive adhesive layer of claim 1 wherein the layer comprises 5 to 95 weight percent pressure-sensitive adhesive component and 5 to 95 weight percent elastomeric material component.

22. The pressure-sensitive adhesive layer of claim 1 wherein the layer comprises 40 to 95 weight percent pressure-sensitive adhesive component and 5 to 60 weight percent tackified elastomeric material component.

23. The pressure-sensitive adhesive layer of claim 1 wherein the layer comprises 5 to 95 weight percent pressure-sensitive adhesive component and 5 to 95 weight percent thermoplastic elastomeric material component.

24. The pressure-sensitive adhesive layer of claim 1 comprising a blend of 40 to 95 weight percent of at least one pressure-sensitive adhesive component and 5 to 60 weight percent of at least one thermoplastic material component selected from the group consisting of polystyrene, amorphous polyester, polymethyl methacrylate and nylon, said layer having an anisotropic peel adhesion.

25. The pressure-sensitive adhesive layer of claim 24 wherein the pressure-sensitive adhesive component is selected from the group consisting of acrylic, styrene block copolymer, natural rubber, synthetic rubber, silicone urea polymer, polyurethane, polyvinylmethylether and blends thereof.

26. The pressure-sensitive adhesive layer of claim 24 wherein the pressure-sensitive adhesive component is styrene block copolymer.

27. A process for producing the pressure-sensitive adhesive layer of claim 1, comprising:
(a) melt mixing said at least one pressure-sensitive adhesive component and said at least one thermoplastic, elastomeric, tackified elastomeric, or thermoplastic elastomeric polymer component,
(b)
  (1) forming said melt blended components into a layer under shear or extensional flow conditions or both or
  (2) forming and drawing said melt blended components, to form said pressure-sensitive adhesive layer, and
(c) allowing said layer to cool.

28. The process of claim 27 wherein the mixing is carried out under dispersive or distributive conditions or a combination thereof.

29. The process of claim 27 wherein the mixing is carried using either a batch or continuous process.

30. The process of claim 29 wherein the batch process is carried out using internal mixing or roll milling.

31. The process of claim 29 wherein the continuous process is carried out using a single screw extruder, a twin screw extruder, a disk extruder, a reciprocating single screw extruder or a pin barrel single screw extruder.

32. A pressure-sensitive adhesive tape comprising a substrate and on the substrate the pressure-sensitive adhesive layer of claim 1.

33. A pressure-sensitive adhesive tape comprising a substrate and on the substrate the pressure-sensitive adhesive layer of claim 24.

34. A pressure-sensitive adhesive electrical tape comprising a polyvinyl chloride substrate or a substrate film of a blend of ethylene-vinyl acetate and ethylene-propylene-diene rubber and on the substrate, a pressure-sensitive adhesive layer comprising a blend of about 5 to 95 weight percent of an acrylic pressure-sensitive adhesive and about 5 to 95 weight percent of a thermoplastic elastomeric block copolymer, said thermoplastic elastomeric block copolymer being immiscible with said pressure-sensitive adhesive, said layer having an anisotropic morphology comprising two axes perpendicular to each other, both parallel to the main surface layer, said axes comprising a longitudinal axis in the film-forming direction and a transverse axis in the cross-web direction, said morphology further comprising at least two distinct domains, a first substantially continuous domain comprising the at least one pressure sensitive adhesive and a second domain comprising the thermoplastic elastomeric block copolymer being fibrillose to schistose in nature and oriented along the film-forming direction.

35. A double coated pressure-sensitive adhesive tape comprising a substrate and on at least one face of the substrate the pressure-sensitive adhesive layer of claim 1 and on any other face of said substrate a pressure-sensitive adhesive.

36. A process for preparing a pressure-sensitive adhesive tape having an pressure-sensitive adhesive layer of claim 1, comprising:
(a) melt mixing said at least one pressure-sensitive adhesive component and said at least one thermoplastic, elastomeric, tackified elastomeric, or thermoplastic elastomeric polymer component,
(b)
  (1) extruding the melt blended components under shear or extensional flow conditions or both onto a substrate or
  (2) extruding and drawing the melt blended components onto a substrate, to form said pressure-sensitive adhesive layer on said substrate, and
(c) allowing said tape to cool.

37. A process for preparing a pressure-sensitive adhesive tape having an pressure-sensitive adhesive layer of claim 1, comprising:
(a) melt mixing said at least one pressure-sensitive adhesive component and said at least one thermoplastic, elastomeric, tackified elastomeric, or thermoplastic elastomeric polymer component to a vessel,
(b)
  (1) forming the melt blended components into a layer under shear or extensional flow conditions or both onto a coextruded substrate or (2) forming and drawing the melt blended components onto a coextruded substrate, said substrate optionally comprising a film forming polymeric resin, to form a coated construction comprising said pressure-sensitive adhesive, and (c) allowing said construction to cool.

38. A process for preparing a pressure-sensitive adhesive tape having an pressure-sensitive adhesive layer of claim 1, comprising:

(a) melt mixing said at least one pressure-sensitive adhesive component and said at least one thermoplastic, elastomeric, tackified elastomeric, or thermoplastic elastomeric polymer component, (b)
  (1) forming the melt blended components into a layer under shear or extensional flow conditions or both or
  (2) forming and drawing the melt blended components, to form said pressure-sensitive adhesive layer(s), said adhesive layer(s) being fed to the outer portions of a feed block having at least three layers and a film forming polymeric resin being fed to a middle portion of said feed block to form a double-coated pressure-sensitive tape, and (c) allowing said tape to cool.

39. A pressure-sensitive adhesive article comprising the pressure-sensitive adhesive of claim 1 in a transdermal drug delivery device.

40. A graphic arts film comprising the pressure-sensitive adhesive of claim 1.

41. A pressure-sensitive adhesive article for adhesion to skin comprising a substrate and on the substrate the pressure-sensitive adhesive of claim 1.

42. The article of claim 41 wherein said substrate is occlusive or non-occlusive.

43. The article of claim 42 wherein said occlusive backing is a film, a foam material, or laminate thereof.

44. The article of claim 42 wherein said non-occlusive backing is a perforated polymeric film, a foam material, a woven fabric or a nonwoven fabric.

* * * * *

UNITED STATES PATENT AND TRADEMARK OFFICE
CERTIFICATE OF CORRECTION

PATENT NO. : 6,632,522 B1
DATED : October 14, 2003
INVENTOR(S) : Hyde, Patrick D.

It is certified that error appears in the above-identified patent and that said Letters Patent is hereby corrected as shown below:

Title page,
Item [57], ABSTRACT,
Line 3, after "and" insert -- the --.

Column 4,
Line 63, delete "$AT^{TM}$" and insert -- $A^{TM}$ --, therefor.

Column 8,
Line 66, after "plasticizers" insert -- , --.

Column 10,
Line 44, after "polyethylene" delete "." insert -- , --, therefor.

Column 11,
Line 10, delete "anisotrdpic" insert -- anisotropic --, therefor.

Column 13,
Line 60, delete "useages" insert -- usages --, therefor.

Column 16,
Line 45, delete "500%" insert -- 100% --, therefor.
Lines 51 and 67, after "2" insert -- , --.

Column 17,
Line 33, after "5" insert -- , --.
Line 50, after "4" insert -- , --.

Column 18,
Line 42, delete "anistropic" and insert -- anisotropic --, therefor.
Line 55, delete "TM" before "2517".

Column 21,
Line 25, delete "34-5" and insert -- 34-35 --, therefor.

Column 22,
Line 30, after "36-39," insert -- , --.

UNITED STATES PATENT AND TRADEMARK OFFICE
CERTIFICATE OF CORRECTION

PATENT NO. : 6,632,522 B1
DATED : October 14, 2003
INVENTOR(S) : Hyde, Patrick D.

It is certified that error appears in the above-identified patent and that said Letters Patent is hereby corrected as shown below:

Column 23,
Line 57, delete "The results are set forth in Table 7." and insert the same on line 56.

Column 25,
Line 12, delete "The results are set forth in Table 9." and insert the same on line 11.
Line 42, after "37" delete ",".
Line 63, after "1" delete ",".

Column 26,
Line 26, delete "specificed" and insert -- specified --, therefor.
Line 34, after "2.0" delete ",".
Line 35, delete "254" delete ",".

Column 27,
Line 27, delete "polymerizd" and insert -- polymerized --, therefor.

Column 28,
Line 49, after "4.6" delete ",".

Signed and Sealed this

Tenth Day of August, 2004

JON W. DUDAS
*Acting Director of the United States Patent and Trademark Office*